United States Patent
Maruyama et al.

(10) Patent No.: US 6,177,454 B1
(45) Date of Patent: Jan. 23, 2001

(54) AMIDE DERIVATIVES AND MEDICINAL COMPOSITIONS THEREOF

(75) Inventors: Tatsuya Maruyama; Kenichi Onda; Masahiko Hayakawa, all of Tsukuba; Takumi Takahashi, Ushiku; Takayuki Suzuki; Tetsuo Matsui, both of Tsukuba, all of (JP)

(73) Assignee: Yamanouchi Pharmaceutical Co., Ltd., Tokyo (JP)

( * ) Notice: Under 35 U.S.C. 154(b), the term of this patent shall be extended for 0 days.

(21) Appl. No.: 09/514,637

(22) Filed: Feb. 29, 2000

Related U.S. Application Data

(62) Division of application No. 09/297,762, filed as application No. PCT/JP98/00237 on Jan. 22, 1998, now Pat. No. 6,048,884.

(30) Foreign Application Priority Data

Jan. 23, 1997 (JP) .................................................. 9-10360

(51) Int. Cl.[7] ................. A61K 31/4184; A61K 31/4174; C07D 233/61; C07D 235/14
(52) U.S. Cl. .......................... 514/394; 514/303; 514/367; 514/368; 514/363; 514/384; 514/400; 546/118; 548/136; 548/154; 548/155; 548/180; 548/263.2; 548/264.2; 548/309.7; 548/338.1
(58) Field of Search .............................. 548/338.1, 309.7, 548/263.2, 264.2, 136, 154, 155, 180; 546/118; 514/400, 394, 303, 384, 363, 368, 367

(56) References Cited

U.S. PATENT DOCUMENTS

| | | | |
|---|---|---|---|
| 5,187,190 | 2/1993 | Lecount | 514/652 |
| 5,541,204 | 7/1996 | Sher et al. | 514/359 |

Primary Examiner—Laura L. Stockton

(74) Attorney, Agent, or Firm—Finnegan, Henderson, Farabow, Garrett & Dunner, L.L.P.

(57) ABSTRACT

An amide derivative represented by the following general formula (I) or a salt thereof and a pharmaceutical composition containing the amide derivative and a pharmaceutically acceptable vehicle.

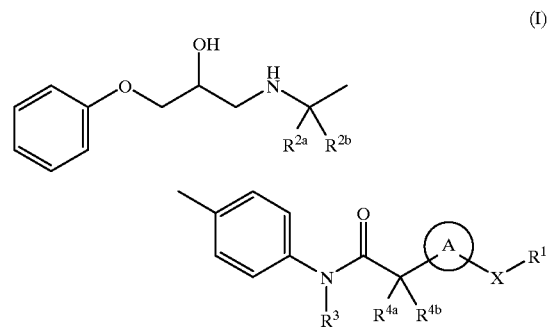

(I)

The symbols in the formula have the following meanings wherein

A: heteroarylene;

X: bond, O, S, —$NR^5$—, —$NR^5CO$—, —$NR^5CONH$—, —$NR^5SO_2$— or —$NR^5C(=NH)NH$—;

$R^1$: —H, -optionally substituted lower alkyl, -optionally substituted aryl, -optionally substituted heteroaryl or -optionally substituted cycloalkyl;

$R^{2a}$, $R^{2b}$: —H or -lower alkyl, which may be the same or different;

$R^3$: —H or -lower alkyl;

$R^{4a}$, $R^{4b}$: —H or —OH, which may be the same different, or $R^{4a}$ and $R^{4b}$ are taken together to form =O or =N—O—lower alkyl; and $R^5$: —H or -lower alkyl.

5 Claims, No Drawings

AMIDE DERIVATIVES AND MEDICINAL COMPOSITIONS THEREOF

This application is a division of application Ser. No. 09/297,762 filed May 7, 1999, now U.S. Pat. No. 6,048,884, which is a 371 of PCT/JP 98/00237 filed Jan. 22, 1998 which is incorporated herein by reference.

TECHNICAL FIELD

The present invention relates to pharmaceuticals, particularly, a pharmaceutical composition containing a novel amide derivative or a salt thereof and a pharmaceutically acceptable vehicle.

BACKGROUND ART

Diabetes mellitus is a disease accompanied by a continuous hyperglycemic state and is said to occur as a result of action of many environmental factors and genetic factors. Main controlling factor for blood sugar is insulin and it has been known that hyperglycemia occurs when insulin becomes deficient or when various factors for inhibiting the action of insulin (such as genetic factor, lack of exercise, obesity and stress) become excessive.

Diabetes mellitus has two main types and is classified into insulin-dependent diabetes mellitus (IDDM) and non insulin-dependent diabetes mellitus (NIDDM). 95% or more of Japanese diabetic patients are said to be NIDDM and an increase in the number of patients due to changes in life style is becoming a problem.

With regard to the therapy of diabetes mellitus, diet therapy, therapeutic exercise and improvement in obesity are mostly conducted in mild cases and, upon progress, administration of oral agent for diabetes (for example, promoters for secretion of insulin such as sulfonylureas and potentiators for insulin sensitivity which potentiate sensitivity of insulin) is conducted. In severer cases, administration of insulin preparations is conducted. However, the above-mentioned insulin secreting action and sensitivity potentiating action are believed to be of an entirely different mechanism and, if compounds which have both of those actions are created, it is expected that they will be the therapeutic agents for diabetes mellitus having new mechanism, having extremely high usefulness and being able to conduct a higher blood sugar control. BRL 35135 [methyl (4-(2-((2-(3-chlorophenyl)-2-hydroxyethyl)amino) propyl)phenoxy)acetate] has been reported as a compound having both those actions (for example, Br. J. Clin. Pharmacol., 42, 291–300, 1996) but its effect is not sufficient and its development as a drug has been ceased already.

On the other hand, substituted phenylsulfonamide derivatives represented by the following general formula are described in EP 611003 and are mentioned to be useful for treating obesity, hyperglycemia, etc. due to their selective stimulating action to $\beta_3$-adrenaline receptor in human being. However, there is no disclosure at all for insulin secretion promoting action and insulin sensitivity potentiating action of those compounds.

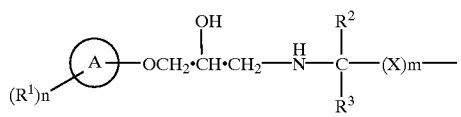

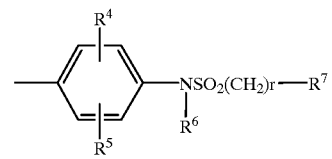

(Refer to the above-mentioned patent for the symbols in the formula.)

DISCLOSURE OF THE INVENTION

The present inventors have conducted an intensive investigation for compounds having both insulin secretion promoting action and insulin sensitivity potentiating action and found that certain novel amide derivatives have both actions of good insulin secretion promoting action and insulin sensitivity potentiating action, leading to accomplishment of the present invention.

That is, the present invention relates to an amide derivative represented by the following general formula (I) or a salt thereof and also relates to a pharmaceutical composition containing the above-described amide derivative or salt thereof and a pharmaceutically acceptable vehicle, particularly a pharmaceutical composition as a therapeutic agent for diabetes mellitus, because the compound has both insulin secretion promoting action and insulin sensitivity potentiating action.

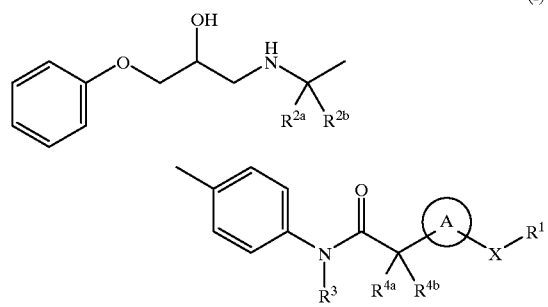

(The symbols in the formula have the following meanings.

A: heteroarylene;

X: bond, O, S, —$NR^5$—, —$NR^5CO$—, —$NR^5CONH$—, —$NR^5SO_2$— or —$NR^5C(=NH)NH$—;

$R^1$: —H, -optionally substituted lower alkyl, -optionally substituted aryl, -optionally substituted heteroaryl or -optionally substituted cycloalkyl;

$R^{2a}$, $R^{2b}$: —H or -lower alkyl, which may be the same or different;

$R^3$: —H or -lower alkyl;

$R^{4a}$, $R^{4b}$: —H or —OH, which may be the same different, or $R^{4a}$ and $R^{4b}$ are taken together to form =O or =N—O—lower alkyl; and $R^5$: —H or -lower alkyl, hereinafter the same.)

In the compound (I) of the present invention, particularly preferred compounds are amide derivatives in which A is thiazolylene, imidazolylene, triazolylene, benzimidazolylene, benzothiazolylene, thiadiazolylene, imidazopyridylene or imidazothiazolylene, and X is a bond, O, S or —NR—, or salts thereof; and amide derivatives in which A is thiazolylene or imidazolylene, X is —$NR^5$—, and $R^1$ is a lower alkyl which is substituted with an optionally substituted aryl, or an optionally substituted aryl, or salts thereof.

Particularly preferred compounds are:

(S)-2-(2-benzylamino-4-thiazol-4-yl)-4'-[2-[(2-hydroxy-3-phenoxypropyl)amino]ethyl]acetanilide;

(S)-2-[2-(3-fluoroanilino)-4-thiazol-4-yl]-4'-[2-[(2-hydroxy-3-phenoxypropyl)amino]ethyl]acetanilide;

(S)-2-(2-anilino-4-thiazol-4-yl)-4'-{2-[(-2-hydroxy-3-phenoxypropyl)amino]propyl}acetanilide; and (S)-2-(2-anilinothiazol-4-yl)-41-{2-[(2-hydroxy-3-phenoxypropyl)amino]ethyl}acetanilide, and salts thereof.

Also, the present invention relates to a pharmaceutical composition containing the amide derivative or salt thereof and a pharmaceutically acceptable vehicle, particularly a pharmaceutical composition as a therapeutic agent for diabetes mellitus.

As hereunder, the compound (I) of the present invention is illustrated in detail.

The term "lower" used in the definitions for the general formula in the present specification means a straight or branched carbon chain having from 1 to 6 carbon atoms unless otherwise mentioned.

The "lower alkyl" is preferably a lower alkyl having from 1 to 4 carbon atoms and is more preferably methyl, ethyl or propyl. The "lower alkenyl" is preferably vinyl. The "lower alkynyl" is preferably ethynyl.

The "aryl" means an aromatic hydrocarbon having from 6 to 14 carbon atoms and is preferably phenyl or naphthyl. The "cycloalkyl" means a saturated hydrocarbon having from 3 to 8 carbon atoms and is preferably cyclohexyl. The "heteroaryl" includes a 5- to 6-membered monocyclic heteroaryl (preferably, furyl, thienyl, imidazolyl, thiazolyl, triazolyl, thiadiazolyl, pyridyl, etc.), a bicyclic heteroaryl in which two 5- to 6-membered heteroaryls are fused (preferably, imidapyridyl, imidazothiazolyl, etc.) and a bicyclic heteroaryl fused with benzene (preferably, benzimidazoyl, benzthiazolyl, etc.).

The "heteroarylene" is a divalent radical in which arbitrary two hydrogen atoms are eliminated from the above-described "heteroaryl" and is preferably thiazolylene, imidazolylene, triazolylene, benzimidazolylene, benzothiazolylene, thiadiazolylene, imidazopyridylene or imidazothiazolylene.

As the substituents of the "optionally substituted aryl", the "optionally substituted heteroaryl", the "optionally substituted cycloalkyl", and the "optionally substituted phenyl", any of ones which are commonly used can be used, and a plurality of substituents which are the same or different may be used. Preferable are substituents selected from -halogen atom(F,Cl,Br,I),-loweralkyl,-loweralkenyl,-loweralkynyl, —OH, —CN, —NO$_2$, —NH$_2$, —CF$_3$, —O-lower alkyl, —COO-lower alkyl, —COOH, —CO-lower alkyl, —NH-lower alkyl, —N(lower alkyl)$_2$, —CONH$_2$, —CONH-lower alkyl, —CO-N(lower alkyl)$_2$, —SO$_2$—NH$_2$, —SO$_2$NH-lower alkyl, —SO$_2$-N(lower alkyl)$_2$, —NHCO-lower alkyl, —NHSO$_2$-lower alkyl, —NHCOO-lower alkyl and —NHCONH-lower alkyl.

As the substituent of the "optionally substituted lower alkyl" can be used -optionally substituted aryl, -optionally substituted heteroaryl and -optionally substituted cycloalkyl, in addition to the substituents as described above.

The "bond" means that no radical is present, but the radicals at the both sides are directly bonded to each other.

Compounds (I) of the present invention have at least one asymmetric carbon atom and, as a result thereof, there are optical isomers such as (R) and (S) compounds, racemic compounds, diastereomers, etc. Further, depending upon the type of the substituent, there may be present geometric isomers based on a double bond, such as (Z) and (E) isomers, and tautomers based on a conjugated double bond. The present invention covers all of those isomers either in a separated form or as a mixture thereof. The present invention further covers hydrates, solvates such as those with ethanol and crystalline polymorphic substances of the compounds (I).

The compounds (I) of the present invention may form a salt with an acid. Examples of such a salt are acid addition salts with mineral acids such as hydrochloric acid, hydrobromic acid, hydroiodic acid, sulfuric acid, nitric acid and phosphoric acid and with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid and glutamic acid.

(Production Methods)

The compounds of the present invention and salts thereof can be prepared by applying various synthetic methods utilizing the characteristics due to the fundamental skeleton or type of the substituents thereof. Representative production methods will be illustrated as hereunder.

First Step

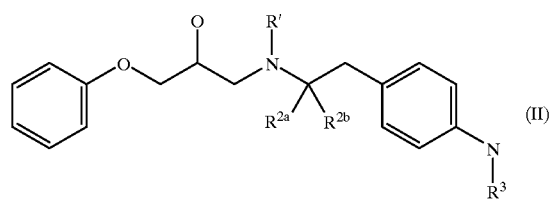

ii) A compound where R$^{4a'}$ and R$^{4b'}$ are taken together to form ═O is subject to reduction reaction, if desired.

-continued

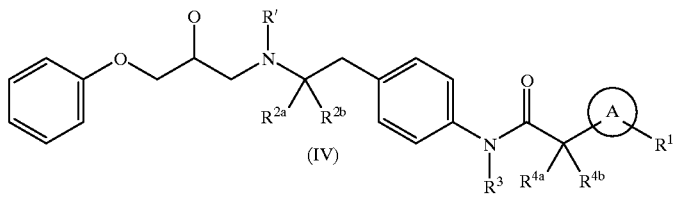

(In the formulae, $R^{4a'}$ and $R^{4b'}$ are a hydrogen atom or are taken together to form =O or =N—O-lower alkyl; and R' is a protective group for amino group, hereinafter the same.)

In this step, i) the compound (II) is reacted with the compound (III) to conduct amidation, whereupon the compound (IV) is synthesized. Alternatively, after the amidation of i), ii) a compound where $R^{4a'}$ and $R^{4b'}$ are taken together to form =O may be subjected to a reduction reaction, if desired, whereupon a compound where $R^{4a}$ is H and $R^{4b}$ is OH is synthesized.

The amidation may be conducted by conventional means. For example, the compounds (II) and (III) either as they are or in a polar solvent are subjected to a reaction in the presence of a condensing agent at room temperature or by heating or under refluxing, whereby the amidation is conducted. As the polar solvent, tetrahydrofuran, dimethylformamide and dimethyl sulfoxide are preferred. As the condensing agent, N,N'-dicyclohexylcarbodiimide, 1-ethyl-3-(3-(N,N-dimethylamino)propyl)carbodiimide hydrochloride, carbonyl imidazole and diphenylphosphoryl azide are preferred.

The "protective group for amino group" of R' means a protective group for amino group commonly used by the persons skilled in the art and preferred examples are -acyl (acetyl, etc.), —CO—O-lower alkyl (t-butoxycarbonyl, etc.), -benzyloxycarbonyl, -benzyl and -Si(lower alkyl)$_3$.

The "lower alkylene" is a divalent radical in which arbitrary two hydrogen atoms are eliminated from the above-described "lower alkyl" and is preferably an alkylene having from 1 to 4 carbon atoms, particularly methylene or ethylene.

In the case of the compound where. $R^{4a'}$ and $R^{4b'}$ are taken together to form =O, the compound where $R^{4a}$ is H and $R^{4b}$ is OH can be synthesized by conducting a reduction reaction. The reduction reaction may be conducted with stirring in the above-mentioned inert solvent in the presence of a reducing agent. Alternatively, catalytic hydrogenation may be conducted in the presence of palladium-on-carbon or the like under atmospheric pressure or elevated pressure.

As the reducing agent, sodium borohydride, sodium cyanoborohydride, etc. are preferred. As the inert solvent, preferred examples are methanol, ethanol, dimethylimidazolidinone, acetic acid, etc. and a mixture thereof and the solvent may be appropriately selected depending upon various reaction conditions.

Also, the compound (II) where $R^3$ is H may be subjected to a conventional N-alkylation reaction to introduce a lower alkyl to $R^3$. Specifically, the compound where $R^3$ is H is reacted with an aldehyde compound (formaldehyde, acetaldehyde, etc.) in an inert solvent in the presence of a reducing agent with stirring under cooling or by heating (under refluxing). Alternatively, catalytic hydrogenation may be conducted in the presence of palladium-on-carbon, platinum oxide or the like under atmospheric pressure or elevated pressure.

Second Step

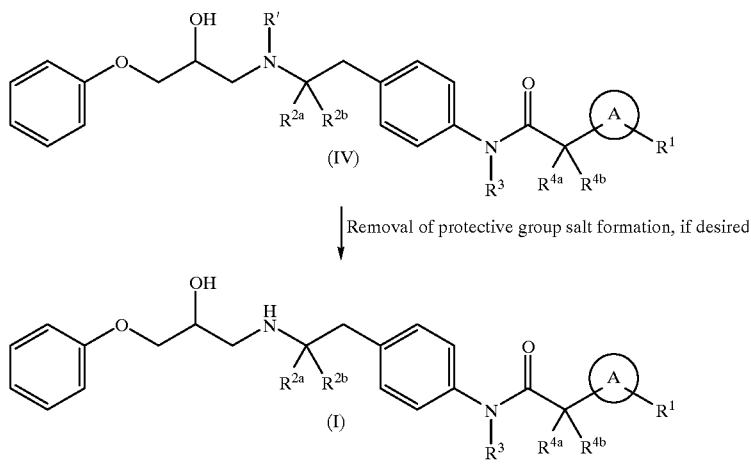

This is a step where the protective group of the compound (IV) is removed to synthesize the compound (I) of the present invention. The removal of the protective group may be conducted according to common means. With regard to the removal of the protective group for amino group, it can be easily carried out by i) a method by treating with an acid such as trifluoroacetic acid and a mixture of hydrochloric acid and dioxane when the protective group is t-butoxycarbonyl or formyl; ii) a catalytic reduction method using palladium-on-carbon or the like when the protective group is benzyl or benzyloxycarbonyl; and iii) a method of treating with water or with fluoride anion (tetra-n-butylammonium fluoride) or the like when the protective group is -Si(lower alkyl)$_3$.

Second Production Method:

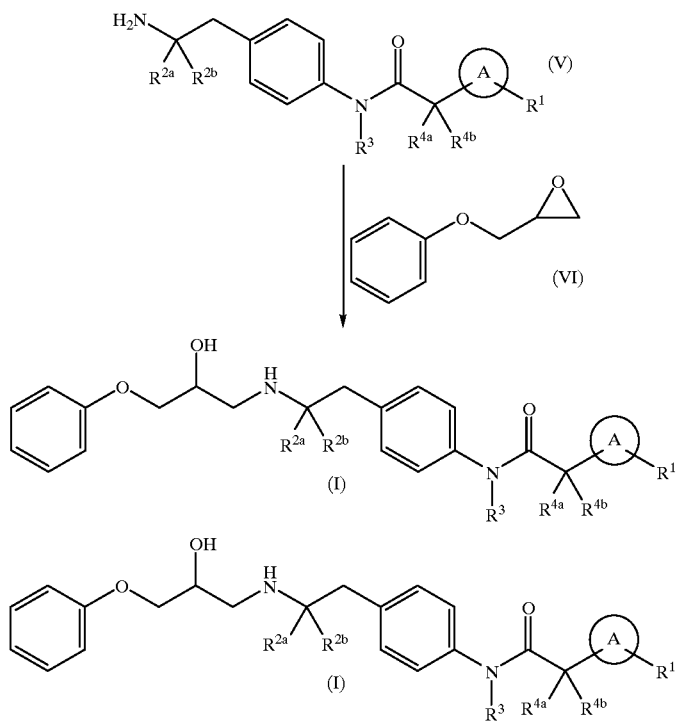

This method is a method in which the amine compound (V) is reacted with the epoxide compound (VI) to synthesize the compound (I) of the present invention. The reaction is a reaction where the amine compound (V) and the epoxide compound (VI) either as they are or in the inert solvent as described above are subjected to coupling for from 1 to 24 hours by heating or under refluxing, preferably by heating at from 30 to 150° C. Alternatively, the synthesis may be carried out by applying the epoxide compound (VI) with a salt (e.g., trifluoroacetate, hydrochloride) of the amine compound (V). In this case, a base such as sodium bicarbonate or diisopropylethylamine may be added to the reaction mixture.

Incidentally, in the above-mentioned respective production methods, it is possible to remove undesired byproducts to purify the prepared substance by means of recrystallization, pulverization, preparatory thin layer chromatography, silica gel flash chromatography as mentioned in W. C. Still, et al., *J. Org. Chem.*, 43, 2923(1978), medium-pressure liquid chromatography or HPLC. The product prepared by HPLC can be isolated as a corresponding salt thereto.

The starting compounds used in the above-mentioned production methods can be easily prepared by methods known by the persons skilled in the art. Representative production methods of the starting compounds are shown as hereunder.

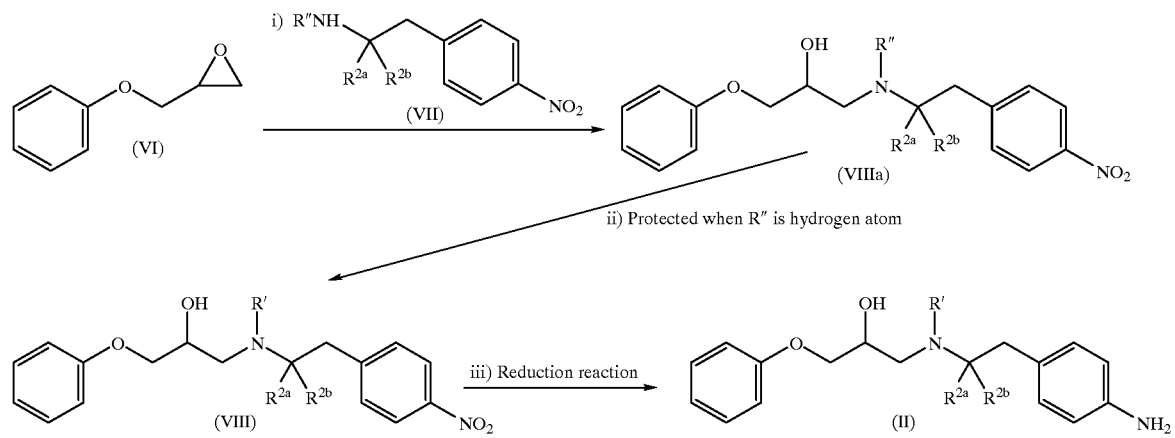

(In the formulae, R″ is a hydrogen atom or an aralkyl-based protective group (for example, -lower alkylene-optionally substituted aryl), hereinafter the same.) This method is a method where i) the compound (VI) is reacted with the compound (VII) to synthesize the compound (VIIIa); ii) protection is conducted when R″ is a hydrogen atom; and iii) a reduction reaction of the compound (VIII) is further conducted, whereupon the compound (II) is synthesized.

The step of i) can be conducted by the same manner as in the second production method and this the same reaction conditions such as reaction temperature and solvent can be applied. The protection of ii) can be conducted by the conventional amino group-protection and it is preferred to use a di-t-butyl dicarbonate or the like. The reduction reaction of iii) can be conducted by metallic reduction, catalytic reduction, etc.

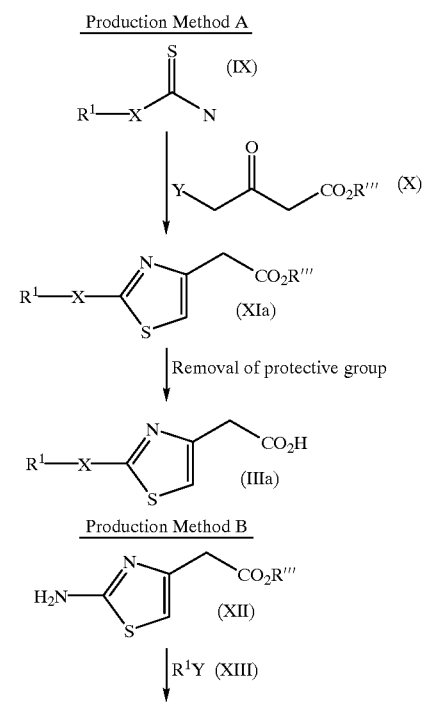

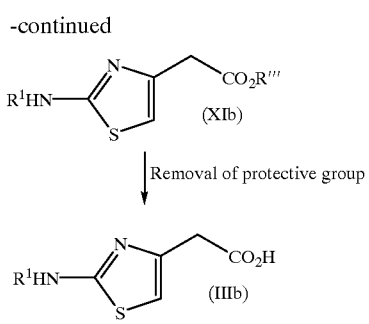

(In the formulae, Y is a halogen atom; and R‴ is a lower alkyl or an aralkyl-based protective group, hereinafter the same.)

Of the compounds (III), substituted thiazolylmethyl-carboxylic acid derivatives can be prepared as follows.

Production Method (A):

The compound (IX) and the compound (X) are reacted in the above-mentioned inert solvent at room temperature or by heating under refluxing, whereby the compound (XIa) can be obtained. When the compound (XIa) is further subjected to hydrolysis, the compound (IIIa) can be obtained. Depending upon the type of the substituents X and $R^1$, the protection and deprotection are necessary and the method therefor can be easily understood by the persons skilled in the art.

Production Method (B):

It is possible to obtain the compound (IIIb) via the compound (XIb) which is prepared from the known 2-aminothiazolyl-4-ylcarboxylic acid ester (XII) by conventional N-alkylation or acylation.

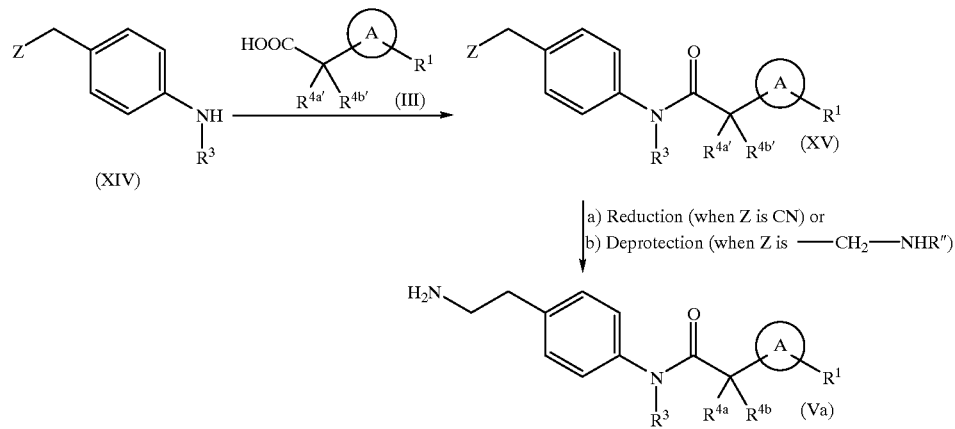

(In the formulae, Z is —CN or —CH$_2$—NHR", hereinafter the same.) This method is a method where the compound (XIV) and the compound (III) are subjected to an amidation reaction to obtain the compound (XV), which is then subjected to a) reduction (when Z is —CN) or b) deprotection (when Z is —CH$_2$—NHR") to obtain the compound (Va).

The amidation reaction between the compound (XIV) and the compound (III) can be conducted in the same manner as in the first step of the first production method as described above. Alternatively, the amidation may be conducted in a conventional manner by using a lower alkyl ester or an aralkyl ester as a reactive derivative of the compound (III) in place of the compound (III). In the reaction from the compound (XV) to the compound (Va), the reduction of a) can be conducted by the conventional catalytic reduction or a method for reduction with cobalt chloride, sodium borohydride or the like. Incidentally, during this reaction, a compound where $R^{4a'}$ and $R^{4b'}$ are taken together to form =O is reduced into a compound where $R^{4a}$ is H and $R^{4b}$ is OH. The deprotection of b) can be conducted in the same manner as in the second step of the first production method as described above.

The compound (I) of the present invention prepared as such can be isolated and purified in a form of free compound, its salt prepared by a conventional salt-forming treatment, hydrate, solvate with various solvents such as ethanol or crystalline polymorphism. The isolation and purification can be conducted by applying common chemical operations such as extraction, concentration, evaporation, crystallization, filtration, recrystallization and various chromatographic means.

Various isomers can be isolated by utilizing the physicochemical difference among the isomers. For example, a racemic compound can be introduced to sterochemically pure isomers by conventional racemic resolution (for example, a method where the racemic compound is introduced into diastereomers with a common optically active acid (tartaric acid, etc., followed by subjecting to optical resolution). In the case of a mixture of diastereomers, the separation can be conducted by a common method such as fractional crystallization or chromatography. Also, optically active compounds can be also prepared using an appropriate optically active starting material.

Applicability of the Invention in Industry

The amide derivatives of the present invention represented by the general formula (I) or salts thereof have both insulin secretion promoting action and insulin sensitivity potentiating action, whereby they are useful as therapeutic agents for diabetes mellitus.

As confirmed by a glucose tolerance test and by a hypoglycemic test in insulin-resisting animal models which will be mentioned later, the compounds of the present invention have both good insulin secretion promoting action and insulin sensitivity potentiating action and are expected to be useful in diabetes mellitus.

Effect of the compounds of the present invention has been confirmed by the following tests.

1. Hypoglycemic test in kk mice (insulin-resisting model: obesity and hyperglycemia) [insulin sensitivity potentiating action]:

Blood sugar levels under feeding were measured for male kk mice (sugar blood level being 200 mg/dl or more) and they were randomly divided into several groups. The drug to be tested was compulsorily administered per os once daily for four days and the blood sugar level after 15 to 18 hours from the final administration was compared with the level prior to the administration (n=6), whereupon a hypoglycemic rate (%) was calculated. Blood was collected from tail vein of the mouse using a glass capillary (previously treated with heparin), protein was removed therefrom and the amount of glucose (mg/dl) in the supernatant liquid was calorimetrically determined by a glucose oxidase method to obtain the blood sugar level.

As a result, the compounds of the present invention significantly lower the blood sugar level as compared with that prior to the administration of the test drug in both cases of oral and subcutaneous administrations and the hypoglycemic rates by oral administration of 10 mg/kg were 47% (p<0.01) for the compound of Example 1, 52% (p<0.01) for the compound of Example 2-b, 50% (p<0.01) of the compound of Example 2-c and 56% (p<0.01) for the compound of Example 4. It is apparent from this result that the compounds of the present invention exhibit good insulin sensitivity potentiating action.

2. Sugar tolerance test in normal rats [insulin secretion promoting action]:

Male rats of SD-strain (seven weeks age) were fasted for one night and day, randomly divided into several groups and subjected to an oral glucose tolerance test (OGTT) (n=4). The compound to be tested was orally administered at 30 minutes before administration of glucose (2 g/kg per os). Blood was collected by a heparin-treated glass syringe from abdominal artery of the rat under anesthetization with 65 mg/kg of pentbarbital, protein was removed therefrom and the amount of glucose (mg/dl) in the supernatant liquid was calorimetrically determined by a glucose oxidase method to obtain the blood sugar level. Insulin level in blood was determined by measuring the amount of insulin (ng/ml) in plasma by means of a radio-immunoassay (RIA). The result was that, when 10 mg/kg of the compound of Example 4 was administered, insulin secretion increased to an extent of three-fold in terms of AUC ratio and blood sugar level decreased to 90% as compared with that prior to the administration. It has been ascertained from this result that the compounds of the present invention exhibit a good insulin secretion promoting action.

In addition, there is possibility that the compounds of the present invention are useful as an antiobesitic agent or a lipid-lowering agent.

A pharmaceutical composition containing one or more of the compounds of the present invention or salts thereof as effective ingredient(s) can be prepared using a common pharmaceutically acceptable vehicle. Administration of the pharmaceutical composition of the present invention may be in any of forms for oral administration and parenteral administration by means of injections, suppositories, percutaneous agents, inhalating agents or intravesical infusions.

Dose may be appropriately decided for each case by taking symptom, age and sex of the patient, etc. into consideration and, usually, it is around 0.01 mg/kg to 100 mg/kg per day for adults in the case of oral administration and this is administered at one time or by dividing into two to four. When intravenous injection is conducted depending upon the symptom, it is administered once or more times a day within a range from 0.001 mg/kg to 10 mg/kg per injection for adults.

With regard to the vehicle for the pharmaceutical preparation, solid or liquid nontoxic substances for pharmaceuticals may be exemplified.

With regard to the solid composition for oral administration in the present invention, tablets, pills, capsules, diluted powder, granules, etc. may be used. In such a solid composition, one or more active substances are mixed with at least one inert diluent such as lactose, mannitol, glucose, hydroxypropyl cellulose, microcrystalline cellulose, starch, polyvinylpyrrolidone, agar, pectin, magnesium metasilicate aluminate and magnesium aluminate. The composition may further contain additives other than the inert diluent, such as lubricants, e.g., magnesium stearate, disintegrating agents, e.g., calcium cellulose glycolate, stabilizers, e.g., lactose, and auxiliary solubilizers, e.g., glutamic acid and aspartic acid, by a conventional method. Tablets or pills may be coated, if necessary, with sugar coat or with film of a substance which is soluble in stomach or in intestine, such as sucrose, gelatin, hydroxypropyl cellulose and hydroxypropylmethyl cellulose phthalate.

Liquid compositions for oral administration cover pharmaceutically acceptable emulsions, solutions, suspensions, syrups, elixiers, etc. and contain commonly used inert diluents such as purified water and ethanol. Such compositions may further contain auxiliary agents such as moisturizers and suspending agents, sweeteners, flavors, aromatic agents, antiseptic agents, etc. in addition to the inert diluent.

Injections for parenteral administration cover sterile aqueous or non-aqueous solutions, suspensions and emulsions. Aqueous solutions and suspensions contain, for example, distilled water for injections and physiological saline solution. Non-aqueous solutions and suspensions contain, for example, propylene glycol, polyethylene glycol, vegetable oils such as cacao butter, olive oil and sesame oil, alcohols such as ethanol, gum arabic, Polysorbate 80 (a trade name), etc. Such compositions may further contain auxiliary agents such as isotonizing agents, antiseptic agents, moisturizers, emulsifiers, dispersing agents, stabilizers (e.g., lactose) and auxiliary solubilizers (e.g., glutamic acid and aspartic acid). They may be sterilized, for example, by filtering through a bacteria-preserving filter, compounding with a bactericide or irradiation. They may also be used by preparing a sterile solid composition, followed by dissolving in sterile water or in a sterile solvent for injections prior to use.

BEST MODE FOR CARRYING OUT THE INVENTION

The present invention is further illustrated by way of the following Examples. The compounds of the present invention are not limited to those which are mentioned in the following Examples and, further, they cover all of the compounds represented by the already-mentioned general formula (I), salts thereof, hydrates thereof, geometrical and optical isomers thereof and crystalline polymorphism. Method for the preparation of the starting material compounds used in the present invention is also given hereunder as Referential Examples.

REFERENTIAL EXAMPLE 1

1.87 g of N-benzylthiourea and 1.82 g of methyl 4-chloroacetoacetate were subjected to a cyclization reaction to obtain 3.10 g of methyl (2-benzylaminothiazol-4-yl)acetate.

REFERENTIAL EXAMPLE 2

3.05 g of methyl (2-benzylaminothiazol-4-yl)acetate was subjected to a hydrolysis reaction to obtain 1.12 g of (2-benzylaminothiazol-4-yl)acetic acid.

REFERENTIAL EXAMPLE 3

0.8 g of methyl 2-(3-sulfanyl-1H-1,2,4-triazol-5-yl) acetate and 0.79 g of benzyl bromide were subjected to an alkylation reaction to obtain 0.79 g of ethyl 2-(3-benzylsulfanyl-1H-1,2,4-triazol-5-yl)acetate.

REFERENTIAL EXAMPLE 4

8.72 g of ethyl 1-benzylimidazol-2-ylacetate hydrochloride was subjected to a debenzylation reaction to obtain 4.74 g of ethyl imidazol-2-ylacetate hydrochloride.

REFERENTIAL EXAMPLE 5

1.07 g of ethyl imidazol-2-ylaceate hydrochloride and 1.69 g of 4-chlorobenzyl bromide were subjected to an alkylation reaction to obtain 0.75 g of ethyl 1-(4-chlorobenzyl)imidazol-2-ylacetate.

REFERENTIAL EXAMPLE 6

15.2 g of 2-methylimidazole and 40.7 g of 4-nitrobenzylimidazole were subjected to an alkylation reaction to obtain 24.8 g of 2-methyl-1-(4-nitrobenzyl) imidazole.

REFERENTIAL EXAMPLE 7

24.8 g of 2-methyl-1-(4-nitrobenzyl)imidazole was reacted with 22 ml of ethyl chloroformate in the presence of 32 ml of triethylamine to obtain 13.9 g of ethyl 1-(4-nitrobenzyl)imidazol-2-ylacetate.

REFERENTIAL EXAMPLE 8

7.71 g of (S)-2-phenoxymethyloxirane and 10.34 g of 2-(4-nitrophenyl)ethylamine hydrochloride were subjected to a ring-opening reaction in the presence of 5.20 g of triethylamine to obtain 6.35 g of (S)-1-phenoxy-3-[[2-(4-nitrophenyl)ethyl]amino]-2-propanol.

REFERENTIAL EXAMPLE 9

6.35 g of (S)-1-phenoxy-3-[[2-(4-nitrophenyl)ethyl]-amino]-2-propanol and 4 g of di-t-butyl dicarbonate were subjected to an acylation reaction to obtain 7.94 g of t-butyl (S)-N-(2-hydroxy-3-phenoxypropyl)-N-[2-(4-nitrophenyl) ethyl]carbamate.

REFERENTIAL EXAMPLE 10

7.94 g of t-butyl (S)-N-(2-hydroxy-3-phenoxypropyl)-N-[2-(4-nitrophenyl)ethyl]carbamate was subjected to a reduction reaction to obtain 5.15 g of t-butyl (S)-N-(2-hydroxy-3-phenoxypropyl)-N-[2-(4-aminophenyl)ethyl]-carbamate.

REFERENTIAL EXAMPLE 11

4.90 g of (S) -1-amino-3-phenoxy-2-propanol and 5.20 g of 4-nitrophenylacetone were subjected to dehydrocondensation and subsequently to a reduction reaction to obtain 8.63 g of (S)-1-[2-[3-[4-nitrophenyl]propyl]amino]-3-phenoxy-2-propanol.

REFERENTIAL EXAMPLE 12

621 mg of t-butyl (S)-N- (2-hydroxy-3-phenoxypropyl)-N-[2-(4-aminophenyl)ethyl]carbamate and 403 mg of 2-(2-methylthiazol-4-yl)acetic acid were subjected to an amidation reaction to obtain 765 mg of t-butyl (S)-N-(2-hydroxy-3-phenoxypropyl)-N-[2-[4-[[2-(2-methylthiazol-4-yl) acetyl]-amino]phenyl]ethyl]carbamate.

REFERENTIAL EXAMPLE 13

2.15 g of t-butyl(S)-N-[(2-hydroxy-3-phenoxy)ethyl]-N-[2-[4-[2-[1-(4-nitrobenzyl)imidazol-2-yl]acetamino]-phenyl]ethyl]carbamate was subjected to a reduction reaction in the presence of 4 ml of a 4N hydrogen chloride-ethyl acetate solution to obtain 960 mg of t-butyl (S)-N-[(2-hydroxy-3-phenoxy)ethyl]-N-[2-[4-[2-(imidazol-2-yl]acetamino]phenyl]-ethyl]carbamate.

REFERENTIAL EXAMPLE 14

340 mg of t-butyl (S)-N-[(2-hydroxy-3-phenoxy)ethyl]-N-[2-[4-[2-(imidazol-2-yl]acetamino]phenyl]ethyl]carbamate and 110 mg of 4-methoxybenzyl chloride were subjected to an alkylation reaction to obtain 160 mg of t-butyl (S)-N-[(2-hydroxy- 3-phenoxy)ethyl]-N-[2-[4-[2-[1-(4-methoxybenzyl)imidazol-2-yl]acetamino]phenyl]ethyl]carbamate.

REFERENTIAL EXAMPLE 15

370 mg of t-butyl (S)-N-(2-hydroxy-3-phenoxypropyl)-N-[2-[4-[[2-(2-aminothiazol-4-yl)-2-oxoacetyl]amino]phenyl]ethyl]carbamate was subjected to a reduction reaction to obtain 290 mg of t-butyl (S)-N-(2-hydroxy-3-phenoxypropyl)-N-[2-[4-[[2-(2-aminothiazol-4-yl)-2-hydroxyacetyl]amino]phenyl]ethyl]carbamate.

REFERENTIAL EXAMPLE 16

960 mg of t-butyl 2-(4-aminophenyl)ethylcarbamate and (2-benzylaminothiazol-4-yl)acetic acid were subjected to an amidation reaction to obtain 500 mg of t-butyl [2-[4-[2-(2-benzylaminothiazol-4-yl)acetylamino]phenyl]ethyl]carbamate.

REFERENTIAL EXAMPLE 17

1.00 g of t-butyl [2-[4-[2-(2-benzylaminothiazol-4-yl)acetylamino]phenyl]ethyl]carbamate was subjected to a deprotection reaction to obtain 690 mg of N-[4-(2-aminoethyl)phenyl]-2-(2-benzylaminothiazol-4-yl)acetamide.

REFERENTIAL EXAMPLE 18

6.40 g of N-methyl-4-cyanomethylaniline was subjected to a reduction reaction to obtain 4.61 g of 2-(4-methylaminophenyl)ethylamine.

REFERENTIAL EXAMPLE 19

2.03 g of 2-(4-methylaminophenyl)ethylamine and 3.20 g of di-t-butylcarbonate were subjected to an acylation reaction to obtain 3.20 g of t-butyl 2-(4-methylaminophenyl)ethylcarbamate.

REFERENTIAL EXAMPLE 20

1.14 g of ethyl 2-(1-methylbenzimidazol-2-yl)acetate and 970 mg of 4-aminobenzylcyanide were subjected to a condensation reaction to obtain 1.19 g of 4'-cyanomethyl-2-(1-methylbenzimidazol-2-yl)acetanilide.

REFERENTIAL EXAMPLE 21

1.15 g of 4'-cyanomethyl-2-(1-methylbenzimidazol-2-yl)acetanilide was subjected to a reduction reaction to obtain 1.11 g of 4'-(2-aminoethyl)-2-(1-methylbenzimidazol-2-yl)acetanilide.

REFERENTIAL EXAMPLE 22

1.52 g of t-butyl (S)-N-[2-(4-aminophenyl)ethyl]-N-(2-hydroxy-3-phenoxypropyl)carbamate and 0.23 g of propionaldehyde were subjected to a reductive amination reaction to obtain 1.69 g of t-butyl (S)-N-(2-hydroxy-3-phenoxypropyl)-N-[2-(4-propylaminophenyl)ethyl]carbamate.

The compounds of Referential Examples 1-a to 21-a shown in the following Tables 1 to 20 were prepared by the same manner as in the above Referential Examples 1 to 21. In the tables, Referential Examples 1-a to 1-n, Referential Examples 2-a to 2-y, Referential Examples 5-a to 5-f, Referential Example 7-a, Referential Examples 9-a (low-polarity material) and 9-b (high-polarity material), Referential Examples 10-a (low-polarity material) and 10-b (high-polarity material), Referential Examples 12-a to 12-ml, Referential Examples 16-a and 16-b, Referential Examples 17-a and 17-b, Referential Example 20-a and Referential Example 21-a were prepared by the same manners as in Referential Examples 1, 2, 5, 7, 9, 10, 12, 16, 17, 20 and 21, respectively.

EXAMPLE 1

A solution of 670 mg of N-[4-(2-aminoethyl)phenyl]-2-(2-benzylaminothiazol-4-yl)acetamide and 300 mg of (S)-2-[(phenoxy)methyl]oxirane in 20 ml of 2-propanol was heated under refluxing for three hours. The solvent was evaporated off in vacuo and the residue was purified by means of silica gel column chromatography (eluate: chloroform/methanol=10/1). The resulting solid was recrystallized from methanol to obtain 250 mg of (S)-2-(2-benzylamino-4-thiazolyl)-4'-[2-[(2-hydroxy-3-phenoxypropyl)amino]ethyl]acetanilide.

EXAMPLE 2

10 ml of a 4N hydrogen chloride-ethyl acetate solution was added to 10 ml of a methanolic solution of 285 mg of t-butyl (S)-N-(2-hydroxy-3-phenoxypropyl)-N-[2-[4-[[2-(2-aminothiazol-4-yl)-2-hydroxyacetyl]amino]phenyl]ethyl]carbamate at room temperature. The reaction mixture was stirred at room temperature for four hours. The solvent was evaporated off and the residue was purified by means of silica gel column chromatography (eluate: chloroform/methanol=7/1) to obtain 222 mg of (S)-4'-[2-[(2-hydroxy-3-phenoxypropyl)amino]ethyl]-2-(2-aminothiazol-4-yl)-2-hydroxyacetanilide dihydrochloride.

EXAMPLE 3

10 ml of a 4N hydrogen chloride-ethyl acetate solution was added to 10 ml of an ethanolic solution of 0.40 g of t-butyl (S)-N-[2-[4-[2-(3-cyanoanilino-4-thiazolyl)acetylamino]phenyl]ethyl]-N-(17-hydroxy-2-phenoxyethyl])carbamate. The mixture was stirred at room temperature overnight and the solvent was evaporated off in vacuo. To the resulting crystals was added 5 ml of methanol-ethanol (4:1), followed by heating and washing. After allowing to stand for cooling, the product was subjected to filtration to obtain 0.18 g of (S)-41-[2-[(2-hydroxy-3-phenoxypropyl)amino]ethyl]-2-[2-(3-cyanoanilino)-4-thiazolyl)]acetanilide dichloride.

EXAMPLE 4

20 ml of methanol and 10 ml of 4N hydrogen chloride-ethyl acetate were added to 470 mg of t-butyl (S)-N-[(2-hydroxy-3-phenoxy)ethyl]-N-[2-[4-[2-(2-phenylaminothiazol-4-yl)acetamino]phenyl]ethyl]carbamate and the mixture was stirred at room temperature for 4.5 hours. The solvent was evaporated off in vacuo and the resulting crude crystals were recrystallized from ethanol-ethyl acetate to obtain 150 mg of (S)-2-(2-phenylaminothiazol-4-yl)-41-[2-[(2-hydroxy-3-phenoxyethyl)amino]ethyl]acetanilide dihydrochloride.

The compounds of Examples 1 to 4-dl shown in the following Tables 21 to 27 were prepared by the same manner as in Examples 1 to 4. In the tables, Examples 1-a to 1-e, Examples 2-a to 2-s, Examples 3-a to 3-i and Examples 4-a to 4-d1 were prepared by the same manners as in Examples 1, 2, 3 and 4, respectively.

As hereunder, chemical structural formulae and physicochemical properties of Referential Examples 1 to 22 are shown in Tables 1 to 20 while chemical structural formulae and physicochemical properties of Examples 1 to 4-d1 are shown in Tables 21 to 27.

Symbols in the tables have the following meanings.

Rf: Referential Example number; Ex: Example number; sal: salt; DATA: physicochemical properties; Str: structural formula; mp: melting point; NMR: nucleomagnetic resonance spectrum [TMS was used as an internal standard and the solvent was DMSO-$d_6$ unless otherwise mentioned]; MS (m/z): mass analytical data (m/z); Me: methyl; Et: ethyl; nPr: n-propyl; iPr: isopropyl; nHex: n-hexyl; Ph: phenyl; Naph: naphthyl; cHex: cyclohexyl; Py: pyridyl; Th: thienyl; Fu: furyl; Boc: t-butoxycarbonyl; 1-Me-1H-Bzim-2-yl: 1-methyl-1H-benzimidazol-2-yl; 1-Bn-1H-Bzim-2-yl: 1-benzyl-1H-benzimidazol-2-yl; 1H-Impy-2-yl: 1H-imidazo[4,5-b]pyridyl-2-yl; 3-Su-1H-Traz-5-yl: 3-sulfanyl-1H-1,2,4-triazol-5-yl; 3-BnSu-1H-Traz-5-yl: 3-benzylsulfanyl-1H-1,2,4-triazol-5-yl; 2-Me-Thdiaz-5-yl: 2-methyl-1,3,4-thiadiazol-5-yl; 1H-Bzim-2-yl: 1H-benzimidazol-2-yl; 1-Bn-1H-Im-4-yl: 1-benzyl-1H-imidazol-4-yl; Imthz-6-yl: Imidazo[2,1-b]thiazol-6-yl; Bzthz-2-yl: benzthiazol-2-yl; 2-(Ph-NH)-Thz-4-yl: 2-phenylaminothiazol-4-yl; and 1-Bn-1H-Im-2-yl: 1-benzyl-1H-imidazol-2-yl.

TABLE 1

| Rf | X | —R$^1$ | sal | DATA |
|---|---|---|---|---|
| 1 | NH | —CH$_2$—Ph | .HCl | NMR δ: 3.55(2H, s), 3.61(3H, s), 4.42(2H, d, J=4.8 Hz), 6.45(1H, s), 7.24–7.36(5H, m), 8.42(1H, brs) |
| 1-b | NH | —(CH$_2$)$_2$—Ph | .HCl | NMR δ: 2.91(2H, t, J=7.0 Hz), 3.64(3H, s), 3.50–3.85 (4H, m), 6.70(1H, s), 7.20–7.50(5H, m) |
| 1-c | NH | —CH$_2$—(3-OMe—Ph) | .HCl | NMR δ: 3.64(3H, s), 3.70(2H, s), 3.74(3H, s), 6.57–6.63 (1H, m), 6.73–6.75(1H, m), 7.02–7.05(1H, m), 7.22–7.26 (1H, m), 7.29–7.30(1H, m), 10.80(1H, brs) |
| 1-d | NMe | —Me | .HCl | NMR δ: 3.22(6H, s), 3.65(3H, s), 3.82(2H, s), 6.81(1H, s) |
| 1-e | NH | -(2-OMe—Ph) | .HCl | NMR (CDCl$_3$) δ: 3.77(2H, s), 3.82(3H, s), 3.92(3H, s), 6.53(1H, s), 6.93–7.05(2H, m), 7.25–7.38(2H, m), 11.15(1H, m) |
| 1-f | NH | -(3-CF$_3$—Ph) | .HCl | NMR (CDCl$_3$) δ: 3.77–3.86(5H, s), 6.62(1H, s), 7.53–7.67(4H, m) |
| 1-g | NH | -(4-CN—Ph) | — | NMR (CDCl$_3$) δ: 3.72(2H, s), 3.76(3H, s), 6.62(1H, s), 7.42–7.50(2H, m), 7.54–7.70(1H, m) |
| 1-h | NH | -(3-OH—Ph) | — | NMR (CDCl$_3$) δ: 3.67(2H, s), 3.74(3H, s), 6.48(1H, s), 6.54(1H, dd, J=2.4, 7.6 Hz), 6.77(1H, dd, J=2.8, 7.6 Hz), 6.92(1H, t, J=2.0 Hz) |
| 1-i | NH | -(3,4-diCl—Ph) | — | NMR (CDCl$_3$) δ: 3.69(2H, s), 3.75(3H, s), 6.53(1H, s), 7.17(1H, dd, J=2.8, 8.8 Hz), 7.35(1H, d, J=8.8 Hz), 7.40(1H, brs), 7.76(1H, s) |
| 1-j | NH | -cHex | — | NMR (CDCl$_3$) δ: 1.14–1.44(5H, m), 1.54–1.66(1H, m), 1.68–1.80(2H, m), 1.98–2.10(2H, m), 3.15–3.30(1H, m), 3.57(2H, s), 3.72(3H, s), 5.10–5.27(1H, br), 6.30(1H, s) |
| 1-k | NH | -(2-Cl—Ph) | .HCl | NMR (CDCl$_3$) δ: 3.63(3H, s), 3.65(2H, s), 6.73(1H, s), 7.03–7.11(1H, m), 7.21–7.36(1H, m), 7.45–7.50(1H, m), 8.13–8.20(1H, m) |
| i-l | NH | -(3-Cl—Ph) | .HCl | NMR (CDCl$_3$) δ: 3.65(3H, s), 3.68(2H, s), 6.75(1H, s), 6.94–7.00(1H, m), 7.31(1H, t, J=8.1 Hz), 7.39–7.45(1H, m,), 7.84(1H, t, J=1.8 Hz), 10.49(1H, brs) |
| 1-m | NH | -(3-CN—Ph) | .HCl | NMR (CDCl$_3$) δ: 3.66(3H, s), 3.70(2H, s), 6.78(1H, s), 7.35–7.39(1H, m), 7.50(1H, t, J=7.8 Hz), 7.76–7.82(1H, m), 8.16–8.19(1H, m), 10.73(1H, brs) |

TABLE 2

| Rf | Str | DATA |
|---|---|---|
| 1-a | 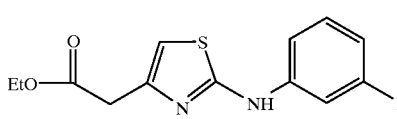 | NMR (CDCl$_3$) δ: 1.34(3H, t, J=7.2 Hz), 3.77(2H, s), 4.28(2H, q, J=7.2 Hz), 6.59(1H, s), 6.98–7.22(3H, m), 7.39–7.49(1H, m) |

TABLE 3

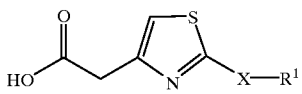

| Rf | X | —X—R¹ | sal | DATA |
|---|---|---|---|---|
| 2 | NH | —CH₂—Ph | .HCl | NMR δ: 3.40(2H, s), 4.39(2H, d, J=6.0 Hz), 6.35(1H, s), 7.23–7.35(5H, m), 8.00(1H, t, J=5.6 Hz), 12.23(1H, brs) |
| 2-a | NH | -(3-F—Ph) | — | NMR δ: 3.58(2H, s), 6.72(1H, s), 6.73–6.79(1H, m), 7.22–7.37(2H, m), 7.64–7.71(1H, m), 10.59(1H, brs) |
| 2-b | NMe | —Me | — | NMR δ: 3.26(6H, s), 3.77(2H, s), 6.83(1H, s), 11.90–12.50(2H, m), 10.00(1H, brs) |
| 2-c | NH | —(CH₂)₂—Ph | — | NMR δ: 2.83(2H, t, J=7.0 Hz), 3.20–3.60(4H, m), 6.34(1H, s), 7.15–7.40(5H, m) |
| 2-d | NH | —CH₂—(3-OMe—Ph) | — | NMR δ: 3.54(2H, s), 3.73(3H, s), 6.46–6.57(1H, m), 6.64(1H, s), 7.07–7.35(2H, m), 7.38(1H, t, J=2.3 Hz), 10.15(1H, brs), 12.30(1H, brs) |
| 2-e | NH | -(2-OMe—Ph) | .HCl | NMR δ: 3.58(2H, s), 3.84(3H, s), 6.68(1H, s), 6.93–7.00 (1H, m), 7.06–7.12(2H, m), 7.93–8.01(1H, m), 10.20(1H, brs) |
| 2-f | NH | -(3-CF₃—Ph) | .HCl | NMR δ: 3.58(2H, s), 6.74(1H, s), 7.25(1H, m), 7.52(1H, t, J=8.0 Hz), 7.76–7.84(1H, m), 8.32(1H, m), 10.53(1H, brs) |
| 2-g | NH | -(3,4-diCl—Ph) | — | NMR δ: 3:57(2H, s), 6.73(1H, s), 7.40–7.55( ), 8.05 (2H, d, J=2.4 Hz), 10.50(1H, brs) |
| 2-h | NH | -(4-CN—Ph) | — | NMR δ: 3.60(2H, s), 6.81(1H, s), 7.70–7.80(4H, m), 10.73(1H, m), 12.38(1H, brs) |
| 2-i | NH | -(3-OH—Ph) | — | NMR δ: 3.53(2H, s), 6.30–6.38(1H, m), 6.61(1H, s), 6.92–7.08(3H, m), 9.33(1H, m), 10.00(1H, brs), 12.32(1H, brs) |
| 2-j | NH | -cHex | — | NMR δ: 3.58(2H, s), 6.74(1H, s), 7.25(1H, m), 7.52(1H, t, J=8.0 Hz), 7.76–7.84(1H, m), 8.32(1H, m), 10.53(1H, brs) |
| 2-k | NH | -(2-Cl—Ph) | .HCl | NMR δ: 3.58(2H, s), 6.75(1H, s), 7.15(1H, dt, J=1.5, 8.1 Hz), 7.36(1H, dt, J=1.5, 8.1 Hz), 7.52(2H, dd, J=1.5, 8.1 Hz), 8.09(2H, d, J=8.1 Hz) |
| 2-l | NH | -(3-Cl—Ph) | .HCl | NMR δ: 3.58(2H, s), 6.72(1H, s), 6.94–7.01(1H, s), 7.30(1H, t, J=8.1 Hz), 7.43–7.48(1H, m), 8.33(1H, t, J=1.8 Hz), 10.58(1H, brs) |
| 2-m | NH | -(3-CN—Ph) | — | NMR δ: 3.59(2H, s), 6.75(1H, s), 7.34–7.39(1H, m), 7.50(1H, t, J=7.8 Hz), 7.75–7.82(1H, m), 8.13–8.17(1H, m), 10.53(1H, brs), 12.37(1H, brs) |

TABLE 4

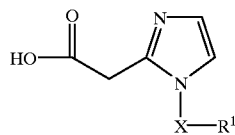

| Rf | X | —R¹ | sal | DATA |
|---|---|---|---|---|
| 2-q | — | —CH₂—(4-Cl—Ph) | .HCl | NMR δ: 4.32(2H, s), 5.45(2H, s), 7.39(2H, d, J=8.8 Hz), 7.46(2H, d, J=8.8 Hz), 7.70(2H, s), 14.00(1H, brs) |
| 2-r | — | —CH₂—(4-CF₃—Ph) | .HCl | NMR δ: 4.32(2H, s), 5.57(2H, s), 7.54(2H, d, J=8.0 Hz), 7.70–7.75(2H, m), 7.77(2H, d, J=8.0 Hz) |
| 2-s | — | —CH₂—(4-Br—Ph) | .HCl | NMR δ: 4.31(2H, s), 5.43(2H, s), 7.32(2H, d, J=8.4 Hz), 7.61(2H, d, J=8.4 Hz), 7.70(2H, s) |
| 2-t | — | —CH₂—(2-Naph) | .HCl | NMR δ: 4.37(2H, s), 5.61(2H, s), 7.45–7.50(1H, m), 7.52–7.60(2H, m), 7.70–7.76(2H, m), 7.8–7.90(4H, m) |
| 2-u | — | —CH₂—(4-F—Ph) | .HCl | NMR δ: 4.33(2H, s), 5.43(2H, s), 7.21–7.27(2H, m), 7.42–7.47(2H, m), 7.68–7.69(2H, m) |
| 2-v | — | —CH₂—(4-I—Ph) | .HCl | NMR δ: 4.31(2H, s), 5.41(2H, s), 7.16(2H, d, J=8.3 Hz), 7.55–7.61(2H, m), 7.76(2H, d, J=8.3 Hz) |
| 2-w | — | —CH₂—(4-iPr—Ph) | .HCl | NMR δ: 1.18(6H, d, J=6.6 Hz), 2.88(1H, sep, 6.6 Hz), 4.32(2H, s), 5.38(2H, s), 7.27(2H, s), 7.66–7.68(4H, m) |
| 2-x | — | —CH₂—(4-NO₂—Ph) | .HCl | NMR δ: 4.32(2H, s), 5.64(2H, s), 7.58(2H, d, J=8.9 Hz), 7.73–7.78(2H, m), 8.25(2H, d, J=8.9 Hz), 14.00(1H, brs) |
| 2-y | — | —Ph | .HCl | NMR δ: 4.16(2H, s), 7.55–7.70(5H, m), 7.88–7.91(1H, m), 7.98–8.00(1H, m) |

TABLE 5

| Rf | Str | DATA |
|---|---|---|
| 2-n | (carboxymethyl-1-benzyl-imidazole ·HCl) | NMR δ: 3.78(2H, s), 5.42(2H, s), 7.38–7.44(6H, m), 7.58(1H, brs), 9.26(1H, brs) |
| 2-o | (carboxymethyl-3-mercapto-1,2,4-triazole ·HCl) | NMR δ: 3.63(2H, s), 12.92(1H, brs), 13.15(1H, brs), 13.32(1H, brs) |
| 2-p | (carboxymethyl-3-benzylthio-1,2,4-triazole ·HCl) | NMR δ: 3.74(2H, s), 4.33(2H, s), 7.20–7.39(5H, m) |
| 3 | (methyl ester of 3-benzylthio-1,2,4-triazolyl acetate) | NMR (CDCl$_3$) δ: 3.78(3H, s), 3.91(2H, s), 4.34(2H, s), 7.20–7.39(5H, m) |
| 4 | (ethyl imidazolyl-2-acetate ·HCl) | NMR δ: 1.22(3H, t, J=6.9 Hz), 4.16(2H, q, J=6.9 Hz), 4.26(2H, s), 7.62(2H, s) |
| 6 | (2-methyl-1-(4-nitrobenzyl)imidazole) | NMR (CDCl$_3$) δ: 2.32(3H, s), 5.19(2H, s), 6.88(1H, d, J=1.4 Hz), 6.98(1H, d, J=1.4 Hz), 7.20(2H, d, J=8.8 Hz), 8.20(2H, d, J=8.8 Hz) |

TABLE 6

(EtO-C(=O)-CH$_2$-imidazolyl-N-X-R$^1$)

| Rf | X | —R$^1$ | sal | DATA |
|---|---|---|---|---|
| 5 | — | —CH$_2$—(4-Cl—Ph) | — | NMR (CDCl$_3$) δ: 1.23(3H, t, J=7.3 Hz), 3.73(2H, s), 4.12(2H, q, J=7.3 Hz), 5.11(2H, s), 6.84(1H, d, J=1.4 Hz), 7.02–7.06(3H, m), 7.30–7.34(2H, m) |
| 5-a | — | —CH$_2$—(4-CF$_3$—Ph) | — | NMR (CDCl$_3$) δ: 1.22(3H, t, J=7.0 Hz), 3.74(2H, s), 4.10(2H, q, J=7.0 Hz), 5.21(2H, s), 6.86(1H, d, J=1.4 Hz), 7.05(1H, d, J=1.4 Hz), 7.20(2H, d, J=9.5 Hz), 7.60(2H, d, J=9.5 Hz) |
| 5-b | — | —CH$_2$—(4-Br—Ph) | — | NMR (CDCl$_3$) δ: 1.13(3H, t, J=6.7 Hz), 4.01(2H, q, J=6.7 Hz), 4.42(2H, s), 5.46(2H, s), 7.31(2H, d, J=8.4 Hz), 7.60(2H, d, J=8.4 Hz), 7.73(1H, d, J=1.5 Hz), 7.77(1H, d, J=1.5 Hz) |
| 5-c | — | —CH$_2$—(2-Naph) | — | NMR (CDCl$_3$) δ: 1.20(3H, t, J=7.3 Hz), 3.76(2H, s), 4.09(2H, q, J=7.3 Hz), 5.29(2H, s), 6.92(1H, d, J=1.4 Hz), 7.05(1H, d, J=1.4 Hz), 7.21–7.26(1H, m), 7.46–7.52(3H, m), 7.75–7.85(3H, m) |
| 5-d | — | —CH$_2$—(4-F—Ph) | — | NMR (CDCl$_3$) δ: 1.23(3H, t, J=7.2 Hz), 3.75(2H, s), 4.13(2H, q, J=7.2 Hz), 5.10(2H, s), 6.84(1H, d, J=1.2 Hz), 7.00–7.12(5H, m) |
| 5-e | — | —CH$_2$—(4-I—Ph) | — | NMR (CDCl$_3$) δ: 1.23(3H, t, J=6.9 Hz), 3.73(2H, s), 4.12(2H, q, J=6.9 Hz), 5.08(2H, s), 6.83–6.86(3H, m), 7.02(1H, d, J=1.5 Hz), 7.67(2H, d, J=8.4 Hz) |
| 5-f | — | —CH$_2$—(4-iPr—Ph) | — | NMR (CDCl$_3$) δ: 1.20–1.26(9H, m), 2.89(1H, sep. J=7.2 Hz), 3.75(2H, s), 4.11(2H, q, J=6.9 Hz), 5.09(2H, s), 6.86(1H, d, J=1.2 Hz), 7.02(2H, d, J=7.2 Hz), 7.19(2H, d, J=7.2 Hz), 7.26(1H, d, J=1.2 Hz) |
| 7 | — | —CH$_2$—(4-NO$_2$—Ph) | — | NMR (CDCl$_3$) δ: 1.23(3H, t, J=6.8 Hz), 3.75(2H, s), 4.12(2H, q, J=6.8 Hz), 5.28(2H, s), 6.87(1H, d, J=1.2 Hz), 7.08(1H, d, J=1.2 Hz), 7.26(2H, d, J=8.4 Hz), 8.22(2H, d, J=8.4 Hz) |

TABLE 6-continued

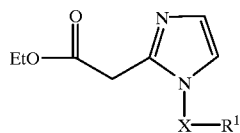

| Rf | X | —R¹ | sal | DATA |
|---|---|---|---|---|
| 7-a | — | —Ph | — | NMR (CDCl₃) δ: 1.19(3H, t, J=7.3 Hz), 3.75(2H, s), 4.12(2H, q, J=7.3 Hz), 7.06(1H, d, J=1.5 Hz), 7.12(1 H, d, J=1.5 Hz), 7.32–7.52(5H, m) |

TABLE 7

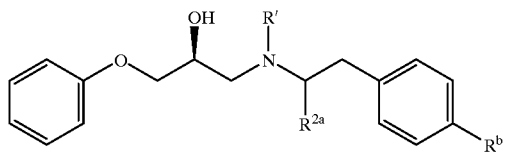

| Rf | —R' | —R²ᵃ | —Rᵇ | DATA |
|---|---|---|---|---|
| 8 | H | H | —NO₂ | NMR (CDCl₃) δ: 2.78–3.01(6H, m), 3.97(2H, d, J=4.9 Hz), 4.01–4.05(1H, m), 6.89(2H, d, J=7.9 Hz), 6.96(1H, t, J=7.3 Hz), 7.27(2H, d, J=7.3 Hz), 7.37(2H, d, J=9.2 Hz), 8.15(2H, d, J=8.6 Hz) |
| 9 | Boc | H | —NO₂ | NMR (CDCl₃) δ: 1.44(9H, s), 2.91–3.05(2H, m), 3.40–3.60(4H, m), 3.85–4.00(2H, m), 4.10–4.20(1H, m), 6.90(2H, d, J=8.0 Hz), 6.98(1H, t, J=7.0 Hz), 7.09–7.32(4H, m), 8.15(2H, d, J=8.8 Hz) |
| 9-a | Boc | —Me | —NO₂ | NMR (CDCl₃) δ: 1.24–1.30(3H, m), 1.35(9H, s), 2.75–3.50(4H, m), 3.80–3.90(1H, m), 3.95–4.30(3H, m), 6.89–7.00(3H, m), 7.23–7.35(4H, m), 8.15(2H, d, J=8.3 Hz) |
| 9-b | Boc | —Me | —NO₂ | NMR (CDCl₃) δ: 1.25–1.28(3H, m), 1.44(9H, s), 2.80–3.40(2H, m), 3.80–3.90(1H, m), 3.95–4.40(3H, m), 6.85–7.00(3H, m), 7.26–7.35(4H, m), 8.12(2H, d, J=8.3 Hz) |
| 10 | Boc | H | —NH₂ | NMR (CDCl₃) δ: 1.46(9H, s), 2.67–2.80(2H, m), 3.30–3.48(4H, m), 3.57(2H, brs), 3.82–4.00(2H, m), 4.06–4.20(2H, m), 6.61(2H, d, J=8.0 Hz), 6.87–7.00(5H, m), 7.25–7.32(2H, m) |
| 10-a | Boc | —Me | —NH₂ | NMR (CDCl₃) δ: 1.18–1.25(3H, m), 1.38(9H, s), 2.50–2.75(2H, m), 3.30–3.60(4H, m); 3.80–4.20(4H, m), 6.57(2H, d, J=8.3 Hz), 6.85–7.00(5H, m), 7.25–7.35(2H, m) |
| 10-b | Boc | —Me | —NH₂ | NMR (CDCl₃) δ: 1.15–1.25(3H, m), 1.45(9H, s), 2.55–4.10(8H, m), 6.55(2H, d, J=8.3 Hz), 6.85–7.00(5H, m), 7.26–7.32(2H, m) |
| 11 | H | —Me | —NO₂ | NMR (CDCl₃) δ: 1.10(3H, d, J=6.4 Hz), 2.68–3.02(5H, m), 3.91–4.02(3H, m), 6.86–6.98(3H, m), 7.28–7.52(4H, m), 8.13–8.18(2H, m) |

TABLE 8

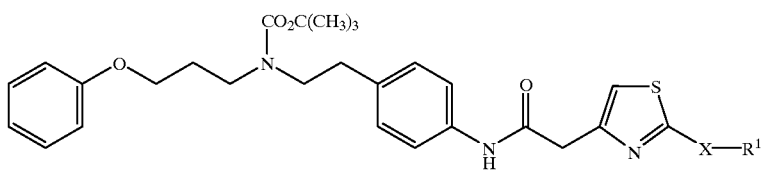

| Rf | X | —R¹ | DATA |
|---|---|---|---|
| 12 | — | —Me | NMR (CDCl₃) δ: 1.46(9H, s), 2.65–2.80(5H, m), 3.30–3.55(4H, m), 3.79(2H, s), 3.85–4.00(2H, m), 4.05–4.20(2H, m), 6.85–7.00(4H, m), 7.05–7.15(2H, m), 7.25–7.30(2H, m), 7.44(2H, d, J=8.4 Hz), 9.07(1H, brs) |

TABLE 8-continued

[Structure: phenoxy-propyl-N(Boc)-ethyl-phenyl-NHC(O)CH2-thiazole-X-R1]

| Rf | X | —R¹ | DATA |
|---|---|---|---|
| 12-a | NH | -Boc | NMR (CDCl₃) δ: 1.46(9H, s), 1.57(9H, s), 2.75–2.86(2H, m), 3.30–3.50(4H, m), 3.71(2H, s), 3.82–4.00(2H, m), 4.09(2H, brs), 6.73(1H, s), 6.89(2H, d, J=7.6 Hz), 6.96(1H, t, J=8.0 Hz), 7.03–7.15(2H, m), 7.29(2H, d, J=7.6 Hz), 7.41(2H, d, J=7.6 Hz), 8.64(1H, brs) |
| 12-b | NH | —Ph | NMR (CDCl₃) δ: 1.49(9H, s), 2.70–2.90(2H, m), 3.30–3.50 (4H, m), 3.69(2H, s), 3.80–4.00(2H, m), 4.11(1H, brs), 6.44(2H, s), 6.89(2H, d, J=8.0 Hz), 6.95(1H, t, J=7.2 Hz), 7.02–7.14(3H, m), 7.24–7.32(2H, m), 7.37–7.44(6H, m), 9.13(1H, s) |
| 12-c | NH | -(3-F—Ph) | NMR (CDCl₃) δ: 1.45(9H, s), 2.71–2.82(2H, m), 3.34–3.48 (4H, m), 3.68(2H, s), 3.83–3.97(2H, m), 4.07–4.16(1H, m), 6.42(1H, s), 6.65–7.45(13H, m), 9.09–9.17(1H, s) |
| 12-h | NH | —Me | NMR (CDCl₃) δ: 1.46(9H, s), 2.65–3.10(5H, m), 3.30–4.25(7H, m), 3.61(2H, s), 6.30(1H, s), 6.80–7.55(9H, m) |
| 12-i | NMe | —Me | NMR (CDCl₃) δ: 1.46(9H, s), 2.70–2.88(2H, m), 3.16(6H, s), 3.30–3.52(4H, m), 3.62(2H, s), 3.80–4.00(2H, m), 4.05–4.16(2H, m), 6.28(1H, s), 6.89(2H, d, J=8.0 Hz), 6.96(1H, t, J=7.2 Hz), 7.03–7.16(2H, m), 7.27–7.30(2H, m), 7.44(2H, d, J=8.8 Hz), 9.77(1H, s) |
| 12-j | NH | —(CH₂)₂—Ph | NMR δ: 1.35(9H, s), 2.72(2H, t, J=7.0 Hz), 2.84(2H, t, J=7.0 Hz), 3.30–3.45(6H, m), 3.49(2H, s), 3.78–4.00(3H, m), 6.35(1H, s), 6.88–7.30(11H, m), 7.51(2H, d, J=8.0 Hz), 7.64(1H, t, J=6.0 Hz) |
| 12-k | NH | -(3-OMe—Ph) | NMR (CDCl₃) δ: 1.46(9H, s), 2.70–2.88(2H, m), 3.30–3.52(4H, m), 3.69(2H, s), 3.82(3H, m), 3.82–4.00(2H, m), 4.05–4.17(2H, m), 6.45(1H, s), 6.67(1H, dd, J1=4.8 Hz, J2=8.0 Hz), 6.89(2H, d, J=8.4 Hz), 6.94–6.96(2H, m), 7.02–7.12(3H, m), 7.21–7.30(3H, m), 7.43(2H, d, J=8.4 Hz), 9.08(1H, s) |
| 12-l | NH | -(2-OMe—Ph) | NMR (CDCl₃) δ: 1.45(9H, s), 2.70–2.82(2H, m), 3.32–3.50(4H, m), 3.75(2H, s), 3.82–3.90(2H, m), 3.92(3H, s), 4.07–4.15(1H, m), 6.44(1H, s), 6.77–7.90(13H, m), 9.24(1H, brs) |
| 12-m | NH | -(2-Cl—Ph) | NMR (CDCl₃) δ: 1.46(9H, s), 2.65–2.80(2H, m), 3.28–3.50(4H, m), 3.72(2H, s), 3.80–3.95(2H, m), 4.10(1H, brs), 6.54(1H, brs), 6.83–7.50(12H, m), 8.12–8.18(1H, m), 8.99(1H, s) |

TABLE 9

[Structure: phenoxy-CH2-CH(OH)-CH2-N(Boc)-ethyl-phenyl-NHC(O)CH2-thiazole-X-R1]

| Rf | X | —R¹ | DATA |
|---|---|---|---|
| 12-n | NH | -(3-Cl—Ph) | NMR (CDCl₃) δ: 1.45(9H, s), 2.72–2.84(2H, m), 3.30–3.50(4H, m), 3.70(2H, s), 3.82–3.99(2H, m), 4.05–4.16(1H, m), 6.47(1H, s), 6.85–7.43(12H, m), 7.58(1H, s), 8.02(1H, brs), 9.11(1H, brs) |
| 12-o | NH | -(3-CN—Ph) | NMR (CDCl₃) δ: 1.45(9H, s), 2.73–2.85(2H, m), 3.35–3.46(4H, m), 3.73(2H, s), 3.82–3.95(2H, m), 4.05–4.16(1H, m), 6.54(1H, s), 6.80–7.84(13H, m), 8.76(1H, s) |
| 12-p | NH | -(3-CF₃—Ph) | NMR (CDCl₃) δ: 1.45(9H, m), 2.67–2.88(2H, m), 3.28–3.52(4H, m), 3.71(2H, s), 3.80–4.00(2H, m), 4.03–4.15(1H, m), 6.51(1H, s), 6.80–7.10(5H, m), 7.20–7.76(8H, m), 8.86(1H, brs) |
| 12-q | NH | -(3,4-diCl—Ph) | NMR (CDCl₃) δ: 1.46(9H, m), 2.70–2.90(2H, m), 3.20–3.50(4H, m), 3.71(2H, s), 3.80–4.00(2H, m), 4.05–4.15(1H, m), 6.51(1H, s), 6.80–7.20(5H, m), 7.25–7.50(6H, m), 7.71(1H, d, J=2.4 Hz), 8.88(1H, brs) |
| 12-r | NH | -(4-CN—Ph) | NMR (CDCl₃) δ: 1.46(9H, m), 2.70–2.90(2H, m), 3.20–3.50(4H, m), 3.74(2H, s), 3.80–4.00(2H, m), 4.03–4.15(1H, m), 6.61(1H, s), 6.80–7.70(13H, m), 8.68(1H, brs) |

TABLE 9-continued

| Rf | X | —R¹ | DATA |
|---|---|---|---|
| 12-s | NH | -(3-OH—Ph) | NMR (CDCl₃) δ: 1.45(9H, m), 2.70–2.90(2H, m), 3.20–3.50(4H, m), 3.65(2H, s), 3.80–4.00(2H, m), 4.05–4.15(1H, m), 6.40(1H, s), 6.55–6.63(1H, m), 6.80–7.50(12H, m), 9.12(1H, brs) |
| 12-t | NH | -cHex | NMR (CDCl₃) δ: 1.25–1.50(14H, m), 1.60–1.70(1H, m), 1.75–1.85(2H, m), 2.00–2.20(2H, m), 2.70–2.90(2H, m), 3.20–3.50(5H, m), 3.65(2H, s), 3.80–4.00(2H, m), 4.05–4.15(1H, m), 6.34(1H, s), 6.80–7.90(9H, m), 7.25–7.50(6H, s), 7.71(1H, d, J=2.4 Hz), 9.30(1H, brs) |
| 12-u | NMe | —Ph | NMR (CDCl₃) δ: 1.45(9H, m), 2.70–2.90(2H, m), 3.20–3.50(4H, m), 3.65(2H, s), 3.80–4.00(2H, m), 4.05–4.15(1H, m), 6.40(1H, s), 6.55–6.63(1H, m), 6.80–7.50(12H, m), 9.12(1H, brs) |
| 12-v | — | —CH₂—(4-OH—Ph) | NMR (CDCl₃) δ: 1.60(9H, s), 2.70–2.85(4H, m), 3.28–3.38(2H, m), 3.78(2H, m), 3.82–3.97(2H, m), 4.15–4.20(1H, m), 4.24(2H, s), 4.61(1H, brs), 6.77(2H, d, J=8.3 Hz), 6.88(2H, d, J=8.8 Hz), 6.94–7.30(10H, m), 7.53(1H, brs), 9.34(1H, brs) |

TABLE 10

| Rf | —R⁴ᵃ | —R⁴ᵇ | DATA |
|---|---|---|---|
| 12-w | =O | | NMR (CDCl₃) δ: 1.46(9H, s), 2.75–2.95(2H, m), 3.35–3.55(4H, m), 3.75–4.00(2H, m), 4.00–4.15(1H, m), 5.46(2H, s), 6.90(2H, d, J=8.4 Hz), 6.96(1H, t, J=7.6 Hz), 7.15–7.31(5H, m), 7.60(2H, d, J=8.4 Hz), 8.80(1H, s), 9.11(1H, s) |
| 15 | —H | —OH | NMR (CDCl₃) δ: 1.46(9H, s), 2.70–2.90(2H, m), 3.30–3.55(4H, m), 3.80–4.00(2H, m), 4.03–4.17(2H, m), 4.29(1H, brs), 4.99(2H, brs), 5.12(1H, d, J=1.2 Hz), 6.66(1H, d, J=1.2 Hz), 6.85–7.00(3H, m), 7.05–7.15(2H, m), 7.25–7.31(2H, m), 7.47(2H, d, J=8.4 Hz), 9.11(1H, brs) |

TABLE 11

| Rf | —A—X—R¹ | DATA |
|---|---|---|
| 12-x | 2-Me-Thdiaz-5-yl | NMR (CDCl₃) δ: 1.46(9H, s), 2.79(3H, s), 2.79–2.85(2H, m), 3.35–3.52(3H, m), 3.75–4.00(2H, m), 4.05–4.15(2H, m), 4.34(2H, s), 6.89(2H, d, J=7.6 Hz), 6.96(1H, t, J=7.2 Hz), 7.06–7.16(2H, m), 7.27–7.30(2H, m), 7.46(2H, d, J=8.4 Hz), 8.79(1H, brs) |

TABLE 11-continued

[Structure: phenoxy-CH2-CH(OH)-CH2-N(CO2C(CH3)3)-CH2CH2-C6H4-NHC(O)-CH2-A-X-R1]

| Rf | —A—X—R¹ | DATA |
|---|---|---|
| 12-y | 1H-Bzim-2-yl | NMR (CDCl$_3$) δ: 1.45(9H, s), 2.75–2.80(2H, m), 3.30–3.55(4H, m), 3.82(2H, s), 3.82–4.00(2H, m), 4.09–4.11(2H, m), 6.88(2H, d, J=8.0 Hz), 6.90–7.00(1H, m), 7.00–7.20(2H, m), 7.20–7.75(8H, m), 9.75–10.05(2H, m) |
| 12-z | Imthz-6-yl | NMR (CDCl$_3$) δ: 1.46(9H, m), 2.70–2.90(2H, m), 3.20–3.50(4H, m), 3.75(2H, s), 3.80–4.00(2H, m), 4.03–4.15(1H, m), 6.51(1H, s), 6.80–7.50(12H, m), 9.28(1H, brs) |
| 12-a1 | 3-Su-1H-Traz-5-yl | NMR (CDCl$_3$) δ: 1.46(9H, s), 2.70–2.88(2H, m), 3.30–3.56(4H, m), 3.75(2H, s), 3.80–3.98(2H, m), 4.05–4.15(1H, m), 6.85–7.50(9H, m), 9.14(1H, s), 12.56(2H, brs) |
| 12-b1 | 3-BnSu-1H-Traz-5-yl | NMR (CDCl$_3$) δ: 1.44(9H, s), 2.68–2.82(2H, m), 3.35–3.50(4H, m), 3.84–3.95(4H, m), 4.07–4.16(1H, m), 4.34(2H, s), 6.83–7.48(14H, m), 9.61(1H, s) |
| 12-c1 | 1-Bn-1H-Im-4-yl | NMR (CDCl$_3$) δ: 1.46(9H, s), 2.78(2H, brs), 3.43(4H, m), 3.62(2H, s), 3.89–3.94(2H, m), 4.11(1H, brs), 5.09(2H, s), 6.80(1H, s), 6.89(2H, d, J=8.3 Hz), 6.98(1H, t, J=7.2 Hz), 7.07(2H, brs), 7.18(2H, dd, J=2.1, 7.2 Hz), 7.26–7.31(2H, m), 7.36–7.40(3H, m), 7.46(2H, d, J=8.3 Hz), 7.56(1H, s) 9.44(1H, brs) |

TABLE 12

[Structure: phenoxy-CH2-CH(OH)-CH2-N(CO2C(CH3)3)-CH2CH2-C6H4-NHC(O)-CH2-(imidazol-2-yl)-N-X-R1]

| Rf | X | —R¹ | DATA |
|---|---|---|---|
| 12-d1 | — | —CH$_2$—(4-Cl—Ph) | NMR (CDCl$_3$) δ: 1.46(9H, s), 2.75–2.87(2H, m), 3.30–3.50(4H, m), 3.71(2H, s), 3.80–4.00(2H, m), 4.05–4.10(1H, m), 5.21(2H, s), 6.89–7.20(10H, m), 7.25–7.30(3H, m), 7.45(2H, d, J=8.3 Hz), 10.15(1H, brs) |
| 12-e1 | — | —CH$_2$—(4-CF$_3$—Ph) | NMR (CDCl$_3$) δ: 1.46(9H, s), 2.75–2.90(2H, m), 3.30–3.50(4H, m), 3.72(2H, s), 3.80–4.00(2H, m), 4.05–4.10(1H, m), 5.25(2H, s), 6.89–6.97(4H, m), 7.09–7.30(7H, m), 7.45(2H, d, J=8.8 Hz), 7.60(2H, d, J=8.3 Hz), 10.05(1H, brs) |
| 12-f1 | — | —CH$_2$—(4-Br—Ph) | NMR (CDCl$_3$) δ: 1.46(9H, s), 2.75–2.85(2H, m), 3.30–3.50(4H, m), 3.70(2H, s), 3.80–4.00(2H, m), 4.05–4.15(1H, m), 5.11(2H, s), 6.89–6.98(6H, m), 7.00–7.15(3H, m), 7.20–7.35(2H, m), 7.40–7.50(4H, m), 10.14(1H, brs) |
| 12-g1 | — | —CH$_2$—(2-Naph) | NMR (CDCl$_3$) δ: 1.46(9H, s), 2.75–2.85(2H, m), 3.30–3.50(4H, m), 3.76(2H, s), 3.80–4.00(2H, m), 4.00–4.05(1H, m), 5.30(2H, s), 6.89–7.12(7H, m), 7.20–7.30(3H, m), 7.44–7.50(5H, m), 7.74–7.83(3H, m), 10.30(1H, brs) |
| 12-h1 | — | —CH$_2$—(4-F—Ph) | NMR (CDCl$_3$) δ: 1.46(9H, s), 2.75–2.85(2H, m), 3.30–3.50(4H, m), 3.80–4.00(4H, m), 4.05–4.10(1H, m), 5.32(2H, s), 6.88–7.16(11H, m), 7.26–7.36(2H, m), 7.59(2H, d, J=8.3 Hz), 9.97(1H, brs) |
| 12-i1 | — | —CH$_2$—(4-I—Ph) | NMR (CDCl$_3$) δ: 1.46(9H, s), 2.75–2.80(2H, m), 3.30–3.50(4H, m), 3.30–3.50(4H, m), 3.72(2H, s), 3.80–4.00(4H, m), 4.05–4.15(1H, m), 5.12(2H, s), 6.82(2H, d, J=8.3 Hz), 6.87–6.98(4H, m), 7.05–7.12(3H, m), 7.28–7.31(2H, m), 7.46(2H, d, J=8.3 Hz), 7.66(2H, d, J=8.3 Hz), 10.08(1H, brs) |
| 12-j1 | — | —CH$_2$—(4-iPr—Ph) | NMR (CDCl$_3$) δ: 1.22(6H, d, J=6.9 Hz), 1.46(9H, s), 2.75–2.85(2H, m), 2.88(1H, sep, J=6.9 Hz), 3.30–3.50(4H, m), 3.80(2H, s), 3.85–4.00(2H, m), 4.05–4.15(1H, m), 5.18(2H, s), 6.89–7.09(9H, m), 7.19(2H, d, J=7.8 Hz), 7.25–7.30(2H, m), 7.53(2H, d, J=8.3 Hz), 10.26(1H, brs) |

TABLE 12-continued

| Rf | X | —R¹ | DATA |
|---|---|---|---|
| 12-k1 | — | —CH₂—(4-NO₂—Ph) | NMR (CDCl₃) δ: 1.47(9H, s), 2.75–2.85(2H, m), 3.30–3.50(4H, m), 3.80–4.00(4H, m), 4.05–4.10(2H, m), 5.50(2H, s), 6.88–6.98(4H, m), 7.05–7.15(3H, m), 7.25–7.75(4H, m), 8.19(2H, d, J=8.8 Hz), 9.78(1H, brs) |
| 12-l1 | — | —Ph | NMR (CDCl₃) δ: 1.47(9H, s), 2.75–2.85(2H, m), 3.35–4.00(4H, m), 3.73(2H, s), 3.80–4.00(2H, m), 4.05–4.10(1H, m), 6.89–7.00(3H, m), 7.10–7.18(4H, m), 7.28–7.30(4H, m), 7.47–7.53(5H, m), 10.44(1H, brs) |

TABLE 13

| Rf | X | —R¹ | DATA |
|---|---|---|---|
| 13 | — | —H | NMR (CDCl₃) δ: 1.46(9H, s), 2.75–2.85(2H, m), 3.30–3.55(4H, m), 3.80–4.00(2H, m), 3.90(2H, s), 4.05–4.15(1H, m), 6.88–6.98(3H, m), 7.00–7.20(4H, m), 7.30–7.40(2H, m), 7.50(2H, d, J=7.8 Hz), 10.027(1H, brs) |
| 14 | — | —CH₂—(4-OMe—Ph) | NMR (CDCl₃) δ: 1.46(9H, s), 2.75–2.80(2H, m), 3.30–4.00(4H, m), 3.74(2H, s), 3.78(3H, s), 3.80–4.00(2H, m), 4.05–4.15(1H, m), 5.07(2H, s), 6.85–7.00(6H, m), 7.00–7.20(5H, m), 7.25–7.30(2H, m), 7.47(2H, d, J=8.8 Hz), 10.34(1H, brs) |

TABLE 14

| Rf | —A—X—R¹ | DATA |
|---|---|---|
| 12-d | 2-(Ph—NH)-Thz-4-yl | NMR (CDCl₃) δ: 1.13–1.25(3H, m), 1.39(9H, s), 2.55–2.80(2H, m), 3.30–3.40(1H, m), 3.60–4.20(5H, m), 3.69(2H, s), 6.44(1H, s), 6.80–7.31(8H, m), 7.36–7.43(6H, m), 9.11(1H, s) |
| 12-e | 1-Bn-1H-Im-2-yl | NMR (CDCl₃) δ: 1.15–1.25(3H, m), 1.39(9H, s), 2.60–4.20(8H, m), 3.75(2H, s), 5.14(2H, s), 6.85–7.00(4H, m), 7.03–7.12(5H, m), 7.26–7.37(5H, m), 7.45–7.50(2H, m), 10.35(1H, s) |
| 12-f | 2-(Ph—NH)-Thz-4-yl | NMR (CDCl₃) δ: 1.13–1.24(3H, m), 1.45(9H, s), 2.60–2.70(1H, m), 3.00–4.20(7H, m), 3.68(2H, s), 6.43(1H, s), 6.80–7.00(4H, m), 7.05–7.15(4H, m), 7.25–7.32(4H, m), 7.36–7.45(6H, m), 9.12(1H, s) |
| 12-g | 1-Bn-1H-Im-2-yl | NMR (CDCl₃) δ: 1.15–1.25(3H, m), 1.46(9H, s), 2.60–4.20(8H, m), 3.71(2H, s), 5.14(2H, s), 6.85–7.00(4H, m), 7.05–7.14(5H, m), 7.26–7.37(5H, m), 7.44–7.48(2H, m), 10.31(1H, s) |

TABLE 15

*Structure: tert-butyl (4-R^b-phenethyl)carbamate*

| Rf | —R^b | DATA |
|---|---|---|
| 16 | *N-methyl-2-[2-(benzylamino)thiazol-4-yl]acetamide* | NMR δ: 1.36(9H, s), 2.62(2H, t, J=6.8 Hz), 3.07–3.21(2H, m), 3.48(2H, s), 4.41(2H, d, J=6.0 Hz), 6.36(1H, s), 6.84(1H, t, J=5.6 Hz), 7.09(2H, d, J=8.8 Hz), 7.22–7.35(5H, m), 7.46(2H, d, J=8.4 Hz), 8.06(1H, t, J=6.0 Hz), 9.97(1H, s) |
| 16-a | *N-methyl-2-(1-benzyl-1H-imidazol-2-yl)acetamide* | NMR (CDCl₃) δ: 1.48(9H, s), 2.75(2H, t, J=6.8 Hz), 3.25–3.40(2H, m), 3.74(2H, s), 4.53(1H, brs), 5.16(2H, s), 6.94(1H, d, J=1.6 Hz), 7.06–7.14(5H, m), 7.29–7.37(3H, m), 7.47(2H, d, J=8.4 Hz), 10.44(1H, s) |
| 16-b | *N,N-dimethyl-2-(1-benzyl-1H-imidazol-2-yl)acetamide* | NMR (CDCl₃) δ: 1.44(9H, s), 2.80(2H, t, J=6.8 Hz), 3.26(3H, s), 3.36–3.38(2H, m), 3.50(2H, s), 5.17(2H, s), 6.81(1H, s), 6.95(1H, s), 7.05(2H, d, J=6.8 Hz), 7.14(2H, d, J=8.0 Hz), 7.22(2H, d, J=8.0 Hz), 7.27–7.33(4H, m) |

TABLE 16

*Structure: 2-(4-R^b-phenyl)ethylamine*

| Rf | —R^b | DATA |
|---|---|---|
| 17 | *N-methyl-2-[2-(benzylamino)thiazol-4-yl]acetamide* | NMR δ: 1.34(1H, brs), 2.57(2H, t, J=6.8 Hz), 2.72(2H, t, J=6.8 Hz), 3.32(1H, brs), 3.48(2H, s), 4.41(2H, d, J=6.0 Hz), 6.36(1H, s), 7.10(2H, d, J=8.4 Hz), 7.21–7.35(5H, m), 7.46(2H, d, J=8.4 Hz), 8.06(1H, t, J=6.0 Hz), 9.96(1H, s) |
| 17-a | *N-methyl-2-(1-benzyl-1H-imidazol-2-yl)acetamide* | NMR (CDCl₃) δ: 1.20(2H, brs), 2.70(2H, t, J=6.8 Hz), 2.93(2H, t, J=6.8 Hz), 3.74(2H, s), 5.15(2H, s), 6.94(2H, d, J=1.2 Hz), 7.07–7.08(3H, m), 7.13(2H, d, J=8.4 Hz), 7.29–7.36(3H, m), 7.47(2H, d, J=8.4 Hz), 10.36(1H, s) |
| 17-b | *N,N-dimethyl-2-(1-benzyl-1H-imidazol-2-yl)acetamide* | NMR (CDCl₃) δ: 1.53(2H, brs), 2.76(2H, d, J=6.8 Hz), 2.98(2H, t, J=6.8 Hz), 3.26(3H, s), 3.50(2H, s), 5.18(2H, s), 6.81(1H, s), 6.95(1H, s), 7.06(2H, d, J=6.0 Hz), 7.14(2H, d, J=8.0 Hz), 7.22–7.33(5H, m) |

TABLE 17

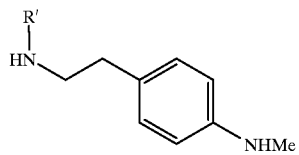

| Rf | —R' | DATA |
|---|---|---|
| 18 | —H | NMR (CDCl$_3$) δ: 1.38(2H, brs), 2.63(2H, t, J=6.8 Hz), 2.81(3H, s), 2.89(2H, t, J=6.8 Hz), 3.50(1H, brs), 6.57(2H, d, J=8.0 Hz), 7.02(2H, d, J=8.0 Hz) |
| 19 | Boc | NMR (CDCl$_3$) δ: 1.43(9H, s), 2.68(2H, t, J=7.6 Hz), 2.83(3H, s), 3.25–3.40(2H, m), 3.64(1H, brs), 4.52(1H, brs), 6.57(2H, d, J=8.4 Hz), 7.03(2H, d, J=8.4 Hz) |

TABLE 18

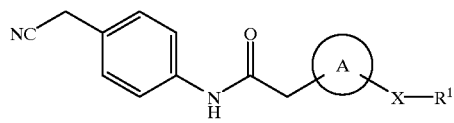

| Rf | —A—X—R$^1$ | DATA |
|---|---|---|
| 20 | 1-Me-1H-Bzim-2-yl | NMR (CDCl$_3$) δ: 3.71(2H, s), 3.83(3H, s), 4.04(2H, s), 7.25–7.40(5H, m), 7.60–7.66(2H, m), 7.74–7.80(1H, m), 10.77(1H, brs) |
| 20-a | 1-Bn-1H-Bzim-2-yl | NMR (CDCl$_3$) δ: 3.71(2H, s), 3.96(2H, s), 5.43(2H, s), 7.03–7.10(2H, m), 7.24–7.38(8H, m), 7.60(2H, d, J=8.8 Hz), 7.78–7.84(1H, m), 10.80(1H, brs) |

TABLE 19

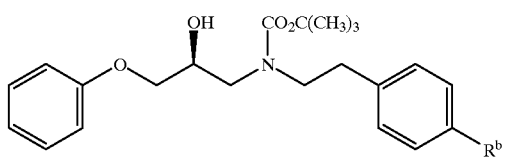

| Rf | —R$^b$ | DATA |
|---|---|---|
| 12-m1 | ![structure: -N(Me)C(=O)CH$_2$-(1-Bn-imidazol-2-yl) with nPr] | NMR δ: 0.81(3H, t, J=7.0 Hz), 1.32(9H, s), 1.30–1.45(2H, m), 2.81(2H, t, J=7.0 Hz), 3.00–3.50(4H, m), 3.26(2H, s), 3.55(2H, t, J=7.0 Hz), 3.75–4.05(3H, m), 5.04(2H, s), 6.50–7.52(16H, m) |
| 22 | —NH-nPr | NMR δ: 0.92(3H, t, J=7.0 Hz), 1.37(9H, s), 1.45–1.75(2H, m), 2.60(2H, t, J=7.0 Hz), 2.91(2H, q, J=7.0 Hz), 2.98–3.40(4H, m), 3.78–4.00(3H, m), 6.80–7.32(7H, m) |

TABLE 20

| Rf | —A—X—R¹ | DATA |
|---|---|---|
| 21 | 1-Me-1H-Bzim-2-yl | NMR (CDCl₃) δ: 2.71(2H, t, J=6.8 Hz), 2.93(2H, t, J=6.8 Hz), 3.83(3H, s), 4.02(2H, s), 7.16(2H, d, J=8.4 Hz), 7.30–7.40(3H, m), 7.50–7.54(2H, m), 7.73–7.80(1H, m), 10.30(1H, brs) |
| 21-a | 1-Bn-1H-Bzim-2-yl | NMR (CDCl₃) δ: 2.70(2H, t, J=6.8 Hz), 2.94(2H, t, J=6.8 Hz), 3.95(2H, s), 5.44(2H, s), 7.00–7.37(10H, m), 7.45–7.53(2H, m), 7.76–7.84(1H, m), 10.37(1H, brs) |

TABLE 21

| Ex | X | —R¹ | sal | DATA |
|---|---|---|---|---|
| 1 | NH | —CH₂—Ph | — | mp: 146–148° C.<br>NMR δ: 2.57–2.75(6H, m), 3.48(2H, s), 3.82–3.94(3H, m), 4.41(2H, d, J=5.6 Hz), 4.94(1H, s), 6.36(1H, s), 6.98–6.93(3H, m), 7.12(2H, d, J=8.4 Hz), 7.21–7.34(8H, m), 7.45(2H, d, J=8.0 Hz), 8.06(1H, t, J=8.0 Hz), 9.96(1H, s) |
| 2-a | NH | —H | 2HCl | mp: 162–165° C.<br>NMR δ: 2.70–3.50(6H, m), 3.65(2H, s), 3.94–4.01(2H, m), 4.23–4.25(1H, m), 5.91(1H, brs), 6.56(1H, s), 6.94–6.97(3H, m), 7.20(2H, d, J=8.0 Hz), 7.28–7.32(2H, m), 7.58(2H, d, J=8.0 Hz), 8.35(1H, brs), 8.91(1H, brs), 9.16(1H, brs), 10.38(1H, s) |
| 2-b | NH | -(3-F—Ph) | 2HCl | NMR δ: 2.96–3.30(6H, m), 3.65(2H, s), 3.92–4.01(2H, m), 4.12–4.23(1H, m), 5.84–5.92(1H, m), 6.72(1H, s), 6.91–6.98(4H, m), 7.19(2H, d, J=8.8 Hz), 7.24–7.45(4H, m), 7.59(2H, d, J=8.3 Hz), 7.90(1H, t, J=2.0 Hz), 8.60–8.80(2H, m), 10.18(1H, s), 10.40(1H, s) |
| 2-g | NMe | —Me | 2HCl | NMR δ: 2.93–3.07(3H, m), 3.12–3.24(3H, m), 3.17(6H, s), 3.72(2H, s), 3.94–4.01(2H, m), 4.21–4.24(1H, m), 6.72(1H, s), 6.94–6.97(3H, m), 7.19(2H, d, J=8.8 Hz), 7.31(2H, t, J=8.4 Hz), 7.58(2H, d, J=8.4 Hz), 8.67(1H, brs), 9.09(1H, brs), 10.39(1H, brs) |
| 2-i | NH | -(2-OMe—Ph) | HCl | NMR δ: 2.88–2.98(2H, m), 2.99–3.08(1H, m), 3.11–3.25(2H, m), 3.61(2H, s), 3.85(3H, s), 3.92–4.01(2H, m), 4.16–4.25(1H, m), 5.89(1H, brs), 6.60(1H, s), 6.81–7.03(6H, m), 7.20(2H, d, J=8.6 Hz), 7.27–7.34(2H, m), 7.58(2H, d, J=8.0 Hz), 8.29(1H, d, J=8.0 Hz), 8.75(1H, brs), 8.86(1H, brs), 9.45(1H, brs), 10.18(1H, s) |

TABLE 22

| Ex | X | —R¹ | sal | DATA |
|---|---|---|---|---|
| 2-j | NH | -(2-Cl—Ph) | HCl | NMR δ: 2.88–3.30(6H, m), 3.62(2H, s), 3.93–4.01(2H, m), 5.89(1H, d, J=5.4 Hz), 6.70(1H, s), 6.93–7.05(4H, m), 7.16–7.59(8H, m), 8.25–8.30(1H, m), 8.60–8.90(2H, m), 9.56(1H, s), 10.15(1H, s) |
| 2-k | NMe | —Ph | HCl | NMR δ: 2.80–3.50(9H, m), 3.59(2H, s), 3.91–4.02(2H, m), 4.13–4.24(1H, m), 5.89(1H, brs), 6.53(1H, s), 6.92–6.99(3H, m), 7.16–7.70(11H, m), 8.60–8.90(1H, br), 10.13(1H, brs) |

TABLE 22-continued

[Structure: phenoxy-CH2-CH(OH)-CH2-NH-CH2-CH2-C6H4-NH-C(=O)-CH2-thiazole-X-R1]

| Ex | X | —R1 | sal | DATA |
|---|---|---|---|---|
| 2-l | NH | -cHex | HCl | NMR δ: 1.10–1.40(5H, m), 1.45–1.70(3H, m), 1.80–2.00(2H, m), 2.80–3.55(9H, m), 3.91–4.03(2H, m), 4.17–4.28(1H, m), 5.91(1H, d, J=4.8 Hz), 6.33(1H, s), 6.80–7.00(3H, m), 7.10–7.70(6H, m), 8.88(1H, brs), 9.10(1H, brs), 10.15(1H, brs) |
| 2-m | NH | -(trans-4-OH-cHex) | 2HCl | NMR δ: 1.20–1.45(4H, m), 1.75–2.00(4H, m), 2.90–4.05(12H, m), 4.20–4.30(1H, m), 6.71(1H, s), 6.92–6.98(3H, m), 7.16–7.24(2H, m), 7.26–7.34(2H, s), 7.56–7.63(2H, m), 8.95(1H, brs), 9.22(1H, brs), 10.59(1H, brs) |
| 2-q | NH | -(4-Cl—Ph) | HCl | NMR δ: 2.86–3.24(6H, m), 3.64(2H, s), 3.92–4.01(2H, m), 4.13–4.22(1H, m), 5.88(1H, d, J=5.4 Hz), 6.68(1H, s), 6.93–6.99(3H, m), 7.20(2H, d, J=8.0 Hz), 7.20(2H, d, J=8.0 Hz), 7.26–7.34(4H, m), 7.58(2H, d, J=8.6 Hz), 7.65(2H, d, J=9.1 Hz), 8.69(1H, brs), 10.16(1H, s), 10.33(1H, s) |
| 2-r | NH | -(4-OMe—Ph) | HCl | NMR δ: 2.85–3.25(6H, m), 3.63(2H, s), 3.70(3H, s), 3.92–4.01(2H, m), 4.13–4.23(1H, m), 5.88(1H, d, J=4.9 Hz), 6.56(1H, s), 6.85(2H, d, J=9.1 Hz), 6.93–6.99(3H, m), 7.20(2H, d, J=8.6 Hz), 7.28–7.34(3H, m), 7.50(2H, d, J=9.1 Hz), 7.58(2H, d, J=8.6 Hz), 8.70–8.90(2H, m), 9.94(1H, s), 10.15(1H, s) |
| 2-s | NH | -(3-Cl—Ph) | HCl | NMR δ: 2.88–3.23(6H, m), 3.90–4.01(2H, m), 4.16–4.26(1H, m), 6.68–6.75(2H, m), 6.93–6.98(3H, m), 7.17–7.35(6H, m), 7.59(2H, d, J=8.3 Hz), 7.75(1H, dt, J=2.4, 12.2 Hz), 8.77(1H, brs), 8.91(1H, brs), 10.21(1H, s), 10.49(1H, s) |
| 3-a | NH | -(3-OMe—Ph) | 2HCl | NMR δ: 2.93–3.10(3H, m), 3.10–3.26(3H, m), 3.66(2H, s), 3.67(3H, s), 3.94–4.01(2H, m), 4.22–4.24(1H, m), 5.71(1H, brs), 6.53(1H, dd, J1=8 Hz, J2=2 Hz), 6.68(1H, s), 6.94–6.97(3H, m), 7.03–7.06(1H, m), 7.15–7.21(3H, m), 7.28–7.40(3H, m), 7.59(2H, d, J=8.8 Hz), 8.87(1H, brs), 9.09(1H, brs), 10.26(1H, s), 10.42(1H, brs) |
| 4 | NH | —Ph | 2HCl | mp: 154–159° C. NMR δ: 2.93–3.04(3H, m), 3.15–3.20(3H, m), 3.66(2H, s), 3.93–4.01(2H, m), 4.20–4.27(1H, m), 6.68(1H, s), 6.94–6.98(4H, m), 7.20(2H, d, J=8.8 Hz), 7.26–7.61(4H, m), 8.87(1H, brs), 9.08(1H, brs), 10.25(1H, s), 10.45(1H, brs) |

TABLE 23

[Structure: phenoxy-CH2-CH(OH)-CH2-NH-CH2-CH2-C6H4-NH-C(=O)-CH2-thiazole-X-R1]

| Ex | X | —R1 | sal | DATA |
|---|---|---|---|---|
| 2-o | NH | -(2-Py) | HCl | mp: 240–245° C. |
| 3 | NH | -(3-CN—Ph) | 2HCl | mp: 166–171° C. |
| 3-f | NH | -(4-NO2—Ph) | HCl | mp: 195–197° C. |
| 3-g | NH | -(4-CF3—Ph) | 2HCl | mp: 227–229° C. |
| 3-h | NH—C(=NH)—NH | —H | 2HCl | mp: >220° C. (decmp.) |
| 3-i | NH—SO2 | —Me | HCl | mp: 249–254° C. |
| 4-a | — | —Me | 2HCl | mp: 208–209° C. (EtOH—Et2O) |
| 4-b | NH | —Me | 2HCl | mp: 203–204° C. |
| 4-c | NH | —(CH2)2—Ph | 2HCl | mp: 214–215° C. |
| 4-h | NH | -(3-CF3—Ph) | 2HCl | mp: 161–163° C. (EtOH—EtOAc) |
| 4-i | NH | -(4-CN—Ph) | 2HCl | mp: 224–225° C. (MeOH—EtOAc) |
| 4-j | NH | -(3-OH—Ph) | 2HCl | mp: 130–134° C. (EtOH—Et2O) |
| 4-k | NH | -(3,4-diCl—Ph) | 2HCl | mp: 190–192° C. (MeOH—EtOAc) |
| 4-t | NH—CO | —Me | HCl | mp: 227–231° C. |
| 4-u | NH—CO | —Ph | HCl | mp: 246–249° C. |

TABLE 23-continued

| Ex | X | —R¹ | sal | DATA |
|---|---|---|---|---|
| 4-v | NH—CO—NH | -nHex | 2HCl | mp: 212–213° C. (MeOH—EtOH) |
| 4-x | NH | -(4-iPr—Ph) | 2HCl | mp: 171–173° C. (EtOH—Et2O) |
| 4-y | NH | -(3-Py) | 2HCl | mp: 232–234° C. (MeOH—EtOH—EtOAc) |
| 4-z | NH | —CH₂—(2-Fu) | 2HCl | mp: 184–189° C. (EtOH—EtOAc) |
| 4-a1 | NH | —CH₂—(2-Th) | 2HCl | mp: 204–207° C. (MeOH—EtOH—EtOAc) |
| 4-b1 | NH | —CH₂—(2-Py) | 2HCl | mp: 129–132° C. (EtOH—EtOAc) |
| 4-c1 | — | —CH₂—(4-OH—Ph) | 2HCl | mp: 190–193° C. (EtOH—EtOAc) |

TABLE 24

| Ex | —R³ | X | —R¹ | sal | DATA |
|---|---|---|---|---|---|
| 1-a | —H | — | —CH₂—Ph | HCl | mp: 175–178° C. |
| 1-d | —CH₃ | — | —CH₂—Ph | 2HCl | NMR δ: 3.07–3.11(3H, m), 3.18–3.26(3H, m), 3.16(3H, s), 3.96–4.03(4H, m), 4.28(1H, brs), 5.34(2H, s), 5.95(1H, brs), 6.92–6.97(3H, m), 7.28–7.45(11H, m), 7.57(1H, d, J=1.6 Hz), 7.63(1H, d, J=1.6 Hz), 9.07(1H, brs), 9.42(1H, brs), 14.66(1H, brs) |
| 2-h | -nPr | — | —CH₂—Ph | 2HCl | NMR δ: 0.82(3H, t, J=7.0 Hz), 1.36–1.46(2H, m), 3.00–4.35(9H, m), 3.56(2H, t, J=7.0 Hz), 3.95(2H, s), 5.34(2H, s), 6.92–7.66(16H, m) |
| 2-n | —H | — | —Ph | 2HCl | NMR δ: 2.90–3.05(3H, m), 3.05–3.25(3H, m), 3.97(2H, t, J=5.4 Hz), 4.10–4.25(3H, m), 5.92(1H, brs), 6.93–6.98(3H, m), 7.18(2H, d, J=8.6 Hz), 7.30(2H, t, J=8.0 Hz), 7.44(2H, d, J=8.0 Hz), 7.60–7.63(5H, m), 7.85(1H, d, J=1.6 Hz), 7.97(1H, d, J=2.2 Hz), 8.90(1H, brs), 9.16(1H, brs), 10.62(1H, s) |
| 3-b | —H | — | —CH₂—(4-OMe—Ph) | 2HCl | mp: 182–190° C. |
| 4-l | —H | — | —CH₂—(4-Cl—Ph) | 2HCl | mp: 200–205° C. (EtOH—EtOAc) |
| 4-m | —H | — | —CH₂—(4-CF₃—Ph) | 2HCl | mp: 200–204° C. (EtOH—EtOAc) |
| 4-n | —H | — | —CH₂—(4-NO₂—Ph) | 2HCl | mp: 217–223° C. (EtOH—EtOAc) |
| 4-o | —H | — | —CH₂—(4-Br—Ph) | 2HCl | mp: 207–210° C. (EtOH—EtOAc) |
| 4-p | —H | — | —CH₂—(2-Naph) | 2HCl | mp: 215–218° C. (EtOH—EtOAc) |
| 4-q | —H | — | —CH₂—(4-F—Ph) | 2HCl | mp: 215–219° C. (EtOH—EtOAc) |
| 4-r | —H | — | —CH₂—(4-I—Ph) | 2HCl | mp: 219–222° C. (EtOH—EtOAc) |
| 4-s | —H | — | —CH₂—(4-iPr—Ph) | 2HCl | mp: 192–194° C. (EtOH—EtOAc) |
| 4-d1 | —H | — | —H | 2HCl | mp: 195–201° C. (EtOH—EtOAc) |

TABLE 25

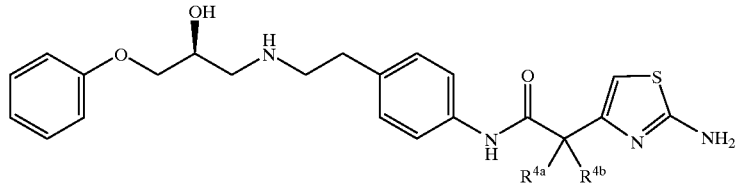

| Ex | —R⁴ᵃ | —R⁴ᵇ | sal | DATA |
|---|---|---|---|---|
| 2 | —H | —OH | 2HCl | NMR δ: 2.88–3.26(6H, m), 3.93–4.10(2H, m), 4.17–4.26(1H, m), 5.11(1H, s), 6.70(1H, s), 6.92–6.99(3H, m), 7.22(2H, d, J=8.8 Hz), 7.31(2H, t, J=8.0 Hz), 7.68(2H, d, J=8.8 Hz), 8.91(1H, brs), 9.15(1H, brs), 10.08(1H, brs) |
| 2-p | =N—OMe | | HCl | NMR δ: 2.91–3.09(3H, m), 3.10–3.26(3H, m), 3.88(3H, s), 3.94–4.03(2H, m), 4.20–4.28(1H, m), 6.88(1H, s), 6.92–6.98(3H, m), 7.23(2H, d), 7.31(2H, t), 7.62(2H, d), 8.89(1H, brs), 9.12(1H, brs), 10.63(1H, brs) |
| 3-e | =O | | 2HCl | mp: 229–233° C. |

TABLE 26

| Ex | —A—X—R¹ | sal | DATA |
|---|---|---|---|
| 1-b | 1-Me-1H-Bzim-2-yl | HCl | mp: 225–226° C. (MeOH—EtOH) |
| 1-c | 1-Bn-1H-Bzim-2-yl | HCl | mp: 226–227° C. (MeOH—EtOH—Et2O) |
| 1-e | 1H-ImPy-2-yl | — | mp: 148–152° C. |
| 3-c | 3-Su-1H-Traz-5-yl | HCl | mp: 178–182° C. |
| 3-d | 3-BnSu-1H-Traz-5-yl | 2HCl | mp: 216–219° C. |
| 4-d | 2-Me-Thdiaz-5-yl | 2HCl | mp: 215–219° C. |
| 4-e | 1H-Bzim-2-yl | 2HCl | mp: 240–245° C. |
| 4-f | 1-Bn-1H-Im-4-yl | 2HCl | mp: 121–123° C. (EtOH—EtOAc) |
| 4-g | Imthz-6-yl | 2HCl | mp: 137–138° C. (MeOH—EtOH—Et₂O) |
| 4-w | Bzthz-2-yl | HCl | mp: 238–240° C. |

TABLE 27

| Ex | —A—X—R¹ | sal | DATA |
|---|---|---|---|
| 2-c | 2-(Ph—NH)—Thz-4-yl | 2HCl | MS (m/z): 517[(M + H)⁺¹] NMR δ: 1.11(3H, d, J=6.2 Hz), 2.58–2.67(1H, m), 3.07–3.23(3H, m), 3.41–3.63(3H, m), 3.95–4.03(2H, m), 4.20–4.25(1H, m), 6.65(1H, s), 6.90–6.98(4H, m), 7.17–7.33(6H, m), 7.25–7.62(4H, m), 8.67(1H, s), 8.79(1H, s), 10.18(1H, s), 10.22(1H, s) |
| 2-d | 1-Bn-1H-Im-2-yl | 2HCl | NMR δ: 1.11(3H, d, J=6.2 Hz), 2.60–2.66(1H, m), 3.00–4.00(4H, m), 3.96–4.04(2H, m), 4.28–4.30(1H, m), 4.44(2H, s), 5.46(2H, s), 6.94–6.98(3H, m), 7.21(2H, d, J=8.3 Hz), 7.29–7.38(7H, m), 7.54(2H, d, J=8.8 Hz), 7.67–7.74(2H, m), 8.85(1H, s), 9.22(1H, s), 10.90(1H, s) |

TABLE 27-continued

| Ex | —A—X—R¹ | sal | DATA |
|---|---|---|---|
| 2-e | 2-(Ph—NH)-Thz-4-yl | 2HCl | NMR δ: 1.14(3H, d, J=6.4 Hz), 2.58–2.65(1H, m), 3.00–3.14(1H, m), 3.20–3.30(2H, m), 3.40–3.50(1H, m), 3.69(2H, s), 3.90–4.10(2H, m), 4.24–4.32(1H, m), 6.71(1H, s), 6.93–7.03(4H, m), 7.20(2H, d, J=8.3 Hz), 7.28–7.33(4H, m), 7.58–7.62(4H, m), 8.81(1H, s), 9.25(1H, s), 10.32(1H, s), 10.69(1H, s) |
| 2-f | 1-Bn-1H-Im-2-yl | 2HCl | NMR δ: 1.13(3H, d, J=6.9 Hz), 2.58–2.67(1H, m), 3.07–3.10(1H, m), 3.24–3.47(3H, m), 3.98–4.02(2H, m), 4.23–4.32(1H, m), 4.43(2H, s), 5.46(2H, s), 6.94–6.98(3H, m), 7.21(2H, d, J=8.3 Hz), 7.29–7.37(7H, m), 7.54(2H, d, J=8.3 Hz), 7.67–7.70(2H, m), 8.78(1H, s), 9.20(1H, s), 10.87(1H, s) |

Compounds other than those as described above are enumerated in the following Tables 28 and 29. These compounds can be synthesized by the above-described production methods or the methods described in the Examples, or by using modified methods which are known to the persons skilled in the art and do no require specific experiments.

TABLE 28

TABLE 28-continued
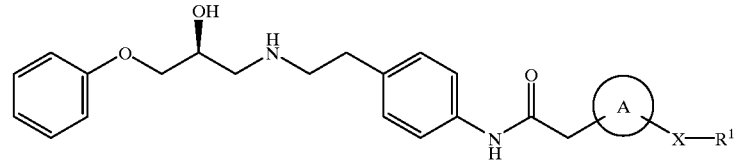
| No. | —A—X—R[1] | No. | —A—X—R[1] |
|---|---|---|---|
| 5 | 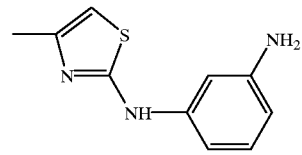 | 15 | 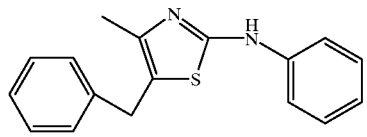 |
| 6 | 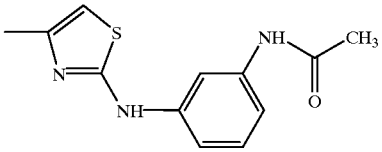 | 16 | 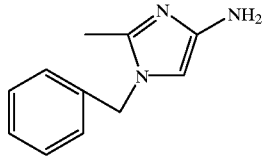 |
| 7 | 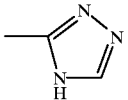 | 17 | 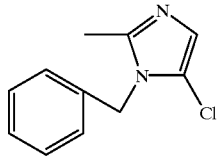 |
| 8 | 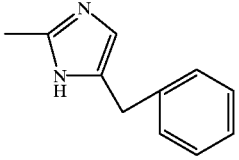 | 18 | 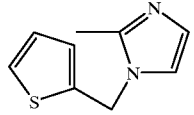 |
| 9 | 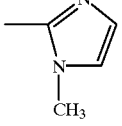 | 19 | 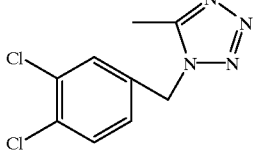 |
| 10 | 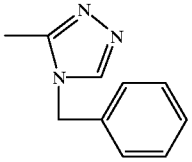 | 20 | 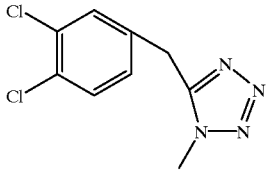 |

TABLE 29

| No. | —R²ᵃ | —R²ᵇ | —R⁴ᵃ | —R⁴ᵇ | —R³ | —A—X—R¹ |
|---|---|---|---|---|---|---|
| 21 | H | H |  | =O | H | 4-methylthiazol-2-yl-NH-phenyl |
| 22 | H | H | OH | H | H | 4-methylthiazol-2-yl-NH-phenyl |
| 23 | H | H | H | H | Me | 2-methylimidazol-1-yl-CH₂-naphthalen-2-yl |
| 24 | H | H | H | H | Me | 4-benzyl-1,2,4-triazol-4-yl |
| 25 | H | H |  | =O | H | 2-methylimidazol-1-yl-benzyl |
| 26 | H | H |  | =O | Me | 2-methylimidazol-1-yl-benzyl |

What is claimed is:

1. An amide derivative represented by the following general formula (I) or a salt thereof:

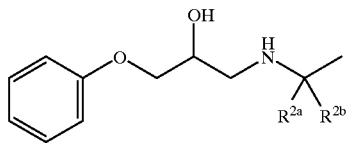

(I)

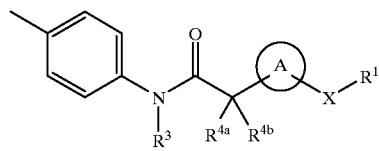

wherein

A: heteroarylene that is not thiazolylene;

X: bond, O, S, —NR⁵—, —NR⁵CO—, —NR⁵CONH—, —NR⁵SO₂— or —NR⁵C(=NH)NH—;

$R^1$: —H, -optionally substituted lower alkyl, -optionally substituted aryl, -optionally substituted heteroaryl or -optionally substituted cycloalkyl;

$R^{2a}$, $R^{2b}$: —H or -lower alkyl, which may be the same or different;

$R^3$: —H or -lower alkyl;

$R^{4a}$, $R^{4b}$: —H or —OH, which may be the same different, or $R^{4a}$ and $R^{4b}$ are taken together to form =O or =N—O-lower alkyl; and $R^5$: —H or -lower alkyl.

2. The amide derivative or salt thereof according to claim 1, wherein A is imidazolylene, triazolylene, benzimidazolylene, benzothiazolylene, thiadiazolylene, imidazopyridylene or imidazothiazolylene; and X is a bond, O, S or —NR$^5$—.

3. The amide derivative or salt thereof according to claim 2, wherein A is imidazolylene; X is —NR$^5$—; and $R^1$ is a lower alkyl which is substituted with an optionally substituted aryl, or an optionally substituted aryl.

4. A pharmaceutical composition containing the amide derivative according to claim 1 and a pharmaceutically acceptable vehicle.

5. A method for treating diabetes mellitus in a human or animal patient in need of such treating, comprising administering to the patient an effective amount of an amide derivative as claimed in claim 1.

* * * * *

UNITED STATES PATENT AND TRADEMARK OFFICE
CERTIFICATE OF CORRECTION

PATENT NO. : 6,177,454 B1
DATED : Jan. 23, 2001
INVENTOR(S) : Maruyama et al.

It is certified that error appears in the above-identified patent and that said Letters Patent is hereby corrected as shown below:

Abstract, Front Page, line 17, change "same different" to --same or different--.

Claim 1, col. 51, line 7, change "same different" to --same or different--.

Signed and Sealed this

Twenty-ninth Day of May, 2001

*Attest:*

NICHOLAS P. GODICI

*Attesting Officer*  *Acting Director of the United States Patent and Trademark Office*